US009366628B2

(12) United States Patent
Crandall et al.

(10) Patent No.: US 9,366,628 B2
(45) Date of Patent: *Jun. 14, 2016

(54) STANDARDIZING FLUORESCENCE MICROSCOPY SYSTEMS

(71) Applicant: Leica Biosystems Imaging, Inc., Vista, CA (US)

(72) Inventors: Gregory Crandall, Vista, CA (US); Allen Olson, Vista, CA (US)

(73) Assignee: LEICA BIOSYSTEMS IMAGING, INC., Vista, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/586,337

(22) Filed: Dec. 30, 2014

(65) Prior Publication Data

US 2015/0204784 A1    Jul. 23, 2015

Related U.S. Application Data

(63) Continuation of application No. 14/232,575, filed as application No. PCT/US2012/046535 on Jul. 12, 2012, now Pat. No. 8,923,568.

(60) Provisional application No. 61/507,352, filed on Jul. 13, 2011.

(51) Int. Cl.
*G01D 18/00* (2006.01)
*G01N 21/64* (2006.01)
(Continued)

(52) U.S. Cl.
CPC ............... *G01N 21/64* (2013.01); *G01J 3/027* (2013.01); *G01J 3/0235* (2013.01); *G01J 3/0264* (2013.01);
(Continued)

(58) Field of Classification Search
CPC . G01N 21/274; G01N 21/276; G02B 21/365; G02B 21/26; G02B 21/367; G06T 7/0044; G06T 7/0018
See application file for complete search history.

(56) References Cited

U.S. PATENT DOCUMENTS 7,072,500 B2    7/2006  Cerrina et al.
7,199,360 B1 *  4/2007  Montagu ................. 250/252.1
(Continued)

FOREIGN PATENT DOCUMENTS

DE         10355164 A1    6/2005
JP        2004529339 A    9/2004
(Continued)

OTHER PUBLICATIONS

"A Standard for Calibration and Shading Correction of a Fluorescence Microscope" Cytometry 44:309-316 (2001) to Model et al.*
(Continued)

*Primary Examiner* — David J Makiya
*Assistant Examiner* — Kenneth J Malkowski
(74) *Attorney, Agent, or Firm* — Procopio Cory Hargreaves and Savitch LLP; Pattric J. Rawlins

(57) ABSTRACT

Systems and methods for standardizing one or more fluorescence scanning instruments to a reference system by separating the effects of drift and normalization. In an embodiment, a drift image comprising an image of a drift reference slide is captured by a system to be standardized. A drift measurement is calculated using the drift image. A first normalization image comprising an image of a normalization slide is also captured by the system to be standardized. A reference normalization image, also comprising an image of the normalization slide, is captured by a reference system. The first normalization image is compared to the reference normalization image to determine a gamma value and offset value for the system to be standardized.

23 Claims, 5 Drawing Sheets

(51) Int. Cl.
- *G06T 5/00* (2006.01)
- *G06T 5/40* (2006.01)
- *G01N 21/27* (2006.01)
- *G02B 21/36* (2006.01)
- *G06T 7/00* (2006.01)
- *G01J 3/44* (2006.01)
- *G01J 3/02* (2006.01)

(52) U.S. Cl.
CPC .............. *G01J 3/4406* (2013.01); *G01N 21/274* (2013.01); *G01N 21/6428* (2013.01); *G01N 21/6458* (2013.01); *G02B 21/365* (2013.01); *G06T 5/009* (2013.01); *G06T 5/40* (2013.01); *G06T 7/0018* (2013.01); *G06T 7/0044* (2013.01); *G01N 21/278* (2013.01); *G01N 21/6452* (2013.01); *G01N 2021/6471* (2013.01); *G06T 2207/10024* (2013.01); *G06T 2207/10056* (2013.01); *G06T 2207/10064* (2013.01)

(56) References Cited

U.S. PATENT DOCUMENTS

| | | | |
|---|---|---|---|
| 7,528,374 B2 | 5/2009 | Smitt et al. | |
| 8,923,568 B2 | 12/2014 | Olson et al. | |
| 2004/0196455 A1 | 10/2004 | Ermantraut et al. | |
| 2007/0147673 A1 | 6/2007 | Crandall | |
| 2007/0159624 A1 | 7/2007 | Resch-Genger et al. | |
| 2008/0178653 A1 | 7/2008 | Gunstream | |
| 2008/0309929 A1* | 12/2008 | Christiansen et al. | 356/243.1 |
| 2009/0002517 A1 | 1/2009 | Yokomitsu et al. | |
| 2009/0153745 A1 | 6/2009 | Park et al. | |
| 2010/0085438 A1 | 4/2010 | Richardson | |

FOREIGN PATENT DOCUMENTS

| | | |
|---|---|---|
| JP | 2007323495 A | 12/2007 |
| JP | 2010530083 A | 9/2010 |
| WO | 2008/156669 A1 | 12/2008 |
| WO | 2013010023 A2 | 1/2013 |

OTHER PUBLICATIONS

International Search Report and Written Opinion of the International Searching Authority issued by Korean Intellectual Property Office, dated Dec. 27, 2012, for related International Application No. PCT/US2012/046535, in 9 pages.

Supplementary European Search Report dated Apr. 7, 2015, for related European Patent Application No. 12811951.8, in 10 pages.

Japan Patent Office, Notice of Reasons for Rejection (with English translation) issued in corresponding JP Application No. 2014-520337, issued Apr. 5, 2016, 9 pages.

\* cited by examiner

STANDARDIZING FLUORESCENCE MICROSCOPY SYSTEMS

RELATED APPLICATION

The present application is a continuation of U.S. patent application Ser. No. 14/232,575, filed on Apr. 22, 2014 and issued as U.S. Pat. No. 8,923,568 on Dec. 30, 2014, which is the U.S. national stage of International App. No. PCT/US2012/46535, filed on Jul. 12, 2012, which claims priority to U.S. Provisional Patent App. No. 61/507,352, filed on Jul. 13, 2011, all of which are hereby incorporated herein by reference in their entireties.

BACKGROUND

1. Field of the Invention

The present invention is generally related to digital pathology and, more particularly, to correcting the sensitivity of a group of similar fluorescence microscopy imaging instruments, as well maintaining the sensitivity of individual instruments over time and/or environmental variations.

2. Related Art

One frequently claimed benefit of fluorescence microscopy is the quantitative nature of signal intensity measurements. Unfortunately, this claimed benefit is commonly misunderstood to imply that fluorescent signals can easily be related back to some absolute intensity standard. In practice, absolute (calibrated) measurements are difficult, if not impossible, to achieve due to the lack of stable, calibrated reference standards.

Fluorescence microscopy system calibration, in terms of absolute sensitivity, requires the use of a calibrated reference standard. Due to difficulties of specimen preparation, and in particular, the unavoidable effect of sample bleaching over time, it is impossible to create a stable, organically based specimen suitable for calibration of a fluorescence microscope. Some stable, inorganic specimens are available, but due to variations in spectral response, these are not suitable for accurate calibration.

Unlike brightfield microscopy, fluorescence signal calibration is complicated by the fact that it is not simply a function of broadband optical transmission. It also has a strong relationship to wavelength. Fluorochromes have been designed to have very narrow spectral response, with their response curves overlapping the steep edges of multiple bandpass filters within the illumination and imaging paths. Even small variation in fluorochrome or filter bandwidths result in changes in the sensitivity of the system. For this reason, it is extremely difficult to predict the overall system sensitivity to a particular fluorochrome based on calibration of individual optical components.

Therefore, what is needed is a system and method that overcomes these significant problems found in conventional systems, as described above.

SUMMARY

The inventors have recognized that in many cases absolute calibration is not required. Instead, standardizing the response of one or more fluorescence instruments may be sufficient. A better approach is to treat the entire device as a system and to measure the end-to-end responsiveness of the system using the fluorochrome(s) needing to be standardized, thereby including the unique spectral characteristics of both the sample and the imaging system. However, the difficulty of signal drift due to sample fading prevents this method from providing a stable reference standard over time. What the inventors have realized is that standardization can be accomplished by separating the effects of normalization and drift.

Other features and advantages of the present invention will become more readily apparent to those of ordinary skill in the art after reviewing the following detailed description and accompanying drawings.

BRIEF DESCRIPTION OF THE DRAWINGS

The structure and operation of the present invention will be understood from a review of the following detailed description and the accompanying drawings in which like reference numerals refer to like parts and in which.

DETAILED DESCRIPTION

Figure 1:
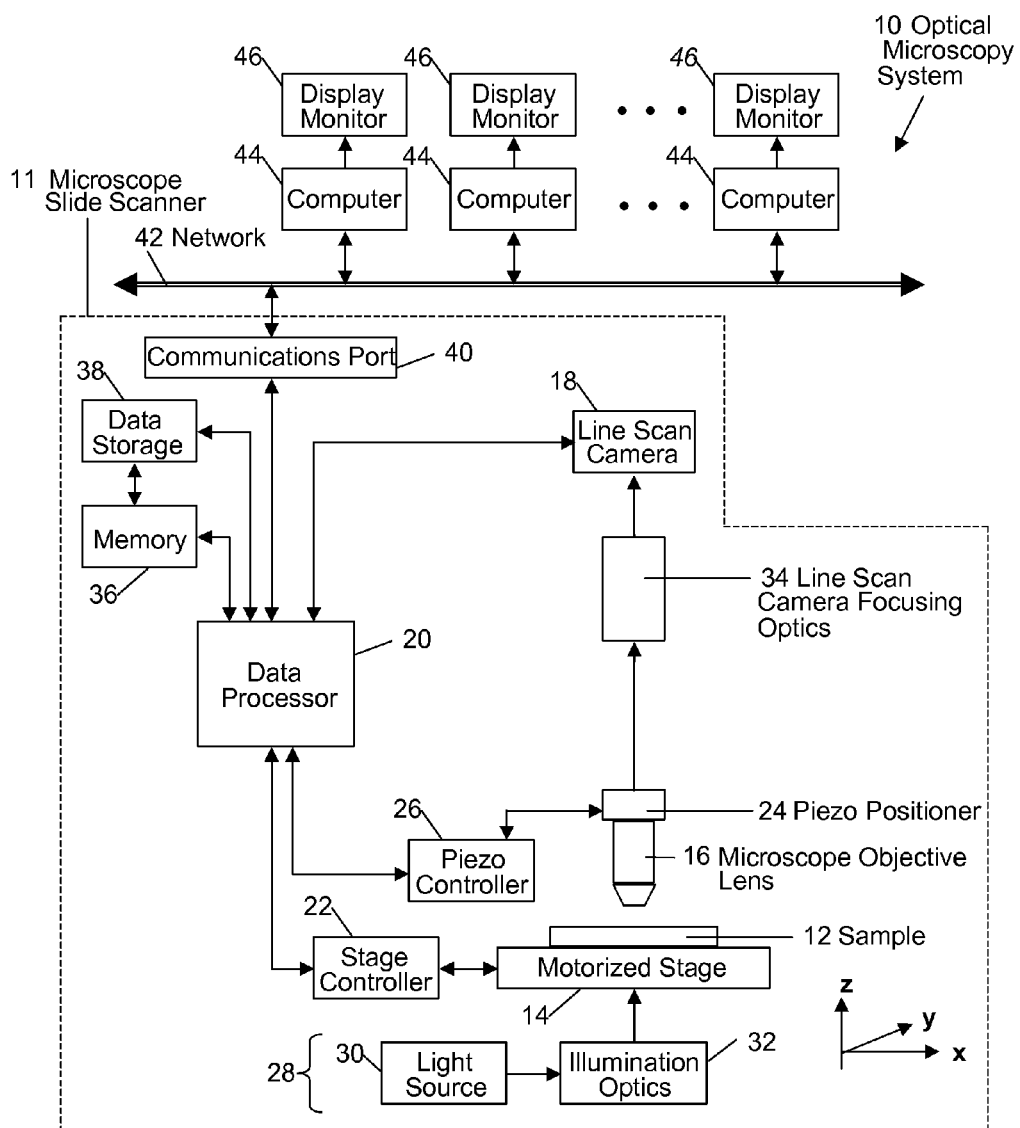
FIG. 1 is a block diagram of a first embodiment of an optical microscopy system according to an embodiment.

Certain embodiments disclosed herein provide for correcting the sensitivity of a group of similar fluorescence microscopy imaging instruments, as well as maintaining the sensitivity of individual instruments over time and/or environmental variations. After reading this description it will become apparent to one skilled in the art how to implement the invention in various alternative embodiments and alternative applications. However, although various embodiments of the present invention will be described herein, it is understood that these embodiments are presented by way of example only, and not limitation. As such, this detailed description of various alternative embodiments should not be construed to limit the scope or breadth of the embodiments of the present invention set forth in the appended claims.

As explained above, the inventors have realized that standardization can be accomplished by separating the effects of normalization and drift.

The following terms have the following definitions herein:

"Standardization" refers to the general process of making two or more systems have identical sensitivities. This can be accomplished in a two step process, comprising normalization and drift correction.

"Normalization" refers to the process of making two or more instruments provide identical results at a particular point in time.

"Drift Correction" refers to the process of making each individual instrument insensitive to variation over time and/or environmental conditions.

The inventors have recognized that separation of these two different aspects of standardization (i.e., normalization and drift correction), enables the use of reference samples that have been optimized for each type of correction. Samples using specific fluorochromes enable inclusion of the effects of filter and fluorochrome bandwith in the calculations to make one system equivalent to another.

Drift, on the other hand, is mostly insensitive to bandwidth variations between systems, and can be accomplished by using readily available broadband reference samples. One example of such samples is colored plastic microscopy slides. These slides, although not suitable for bandwidth specific standardization, are extremely stable over time, and provide a broadband spectral response suitable for measuring instrument sensitivity drift over time.

Image Standardization

In one embodiment, two or more fluorescence microscopy imaging instruments, A and B, are to be standardized so that intensities derived from each system are equivalent. In this example, A is the reference system, and B is the standardized system. The goal is to derive a formula which, when applied to image pixel intensities from system B at time t, will correct each intensity to what would have been obtained on system A, at exposure $T_A(0)$ at time 0.

$$I_A(0) = f[I_B(t)]$$

Variables:

$I_A(0)$=equivalent pixel intensity of System A, at a time 0;
$I_B(t)$=pixel intensity from System B, at a time (t);
$G_B$=Gamma of system B relative to A (constant over time);
$O_B$=Offset of system B relative to A (constant over time);
$D_B(0)$=Drift Factor of system B at time 0;
$D_B(t)$=Drift Factor of system B at time t;
$T_B(0)$=Tissue exposure of system B at time 0; and
$T_B(t)$=Tissue exposure of system B at time t.

Derivation:

For two linear systems, A and B, define a gamma $G_B$ and an offset $O_B$ which relate intensity measurements between system B and system A at time 0 as follows:

$$IB(0) = \frac{I_A(0)}{G_B} + OB \qquad \text{equation (1)}$$

Notably, at time 0, although each system may have acquired images at unique exposures, it is not necessary to explicitly include exposure corrections in equation (1), because any possible exposure difference is already included in G and 0.

For a particular system, if the sensitivity of that system drifts over time (e.g., due to light source degradation), then the intensity at time t can be extrapolated from intensity at time 0 by knowing the sensitivity D at time 0 and time t, and correcting for any exposure variations T.

$$I(t) = I(0) * \left[\frac{D(t)}{D(0)}\right] * \left[\frac{T(t)}{T(0)}\right] \qquad \text{equation (2)}$$

Using equation (1) to substitute for 1(0) in equation (2) gives the following, which relates system B to system A at any time t:

$$IB(t) = \left(\left[\frac{I_A(0)}{G_B}\right] + OB\right) * \left[\frac{D_B(t)}{D_B(0)}\right] * \left[\frac{T_B(t)}{T_B(0)}\right] \qquad \text{equation (3)}$$

Solving for $I_A(0)$ in equation (3) gives the desired relationship between $I_B(t)$ and $I_A(0)$:

$$IA(0) = GB * \left(IB(t) * \left[\frac{D_B(0)}{D_B(t)}\right] * \left[\frac{T_B(0)}{T_B(t)}\right] - OB\right) \qquad \text{equation (4)}$$

Accordingly, using equation (4) enables standardization of fluorescence microscopy systems by determining each of the correction parameters.

Practical Application

Figure 6:
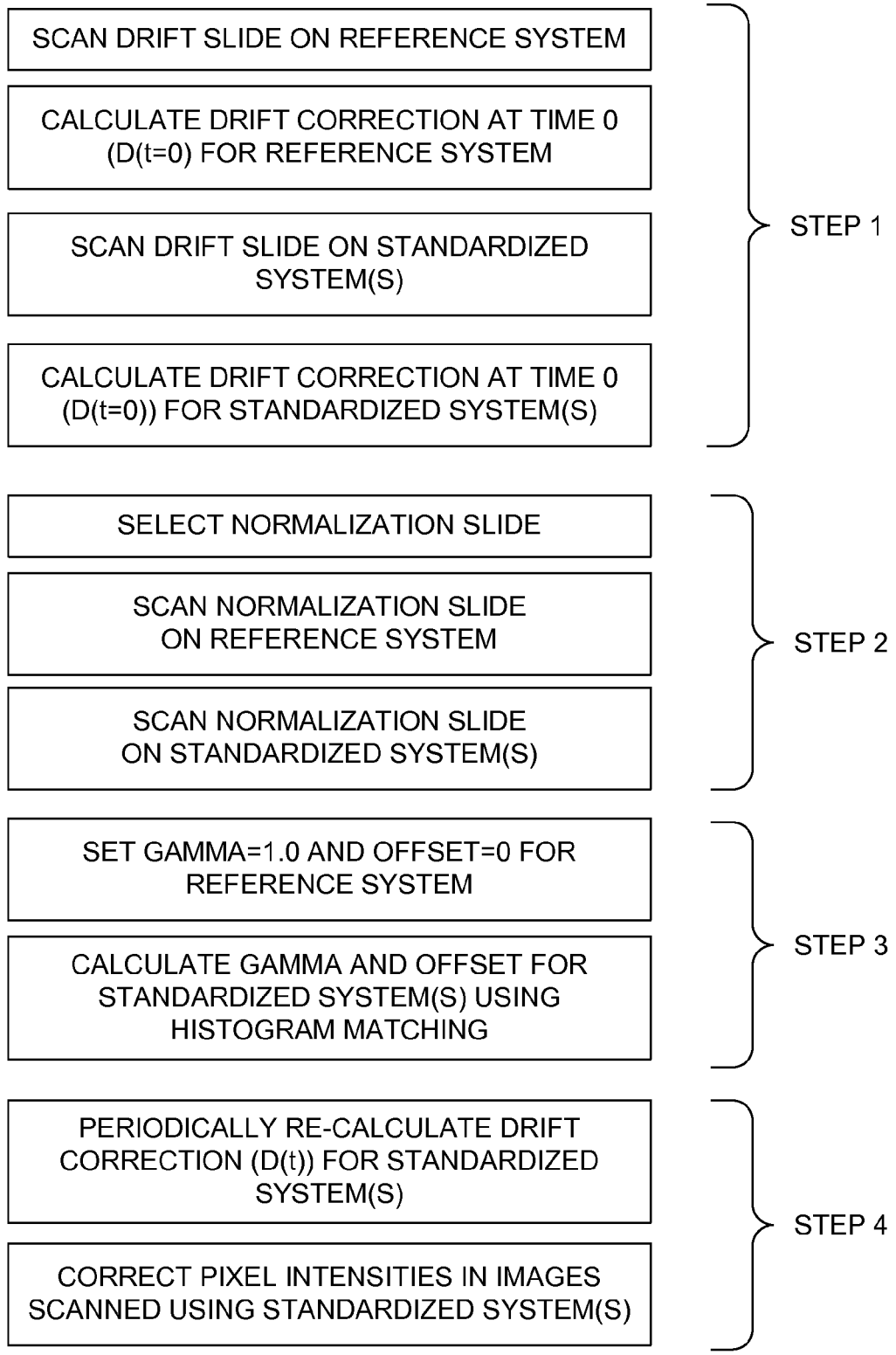
FIG. 6 is a flow diagram illustrating an example process for standardizing a fluorescence scanning instrument, according to an embodiment.

FIG. 6 is a flow diagram illustrating an example process for standardizing a fluorescence scanning instrument, according to an embodiment. In an embodiment, the process begins with capturing the initial drift reference followed by instrument normalization for each system. A first system is defined as the reference system (System A). All remaining systems (Systems B, C, etc.) are standardized to the reference system.

Step (1) Initial Drift Reference:

A drift reference image is captured using a colored plastic or other suitable "Drift Slide." The Drift reference for system A at time 0, $D_A(0)$, is calculated per the following:

$$DA(0) = \text{average pixel intensity/exposure} \qquad \text{equation (5)}$$

Notably, although each instrument may use a different drift slide, all subsequent drift captures for each instrument should be performed with the slide used for its initial drift reference.

Step (1) is repeated for each instrument in turn, calculating initial drift references for each instrument. Step (2) should be completed as soon as possible in order to minimize any instrument drift between Steps (1) and (2).

Step (2) Normalization:

A slide is selected for the normalization procedure. This slide will be imaged once by each system to be normalized. This specimen should be well prepared, and representative of the fluorochrome(s) to be standardized. It should have a broad range of pixel intensities, similar to the samples to be measured. It should also be as stable as possible with respect to photobleaching caused by multiple exposures. It does not have to be stable over long periods of time, as it will not be needed after the initial instrument normalizations are completed.

An image of the normalization reference slide is captured. This image is used to determine a gamma and offset for each system. The same region of the reference slide should be captured for each instrument. Variations of the region can increase correction inaccuracy.

Step (3) Calculation of Gamma and Offset:

Each system will have an associated gamma and offset, specific to that system. It will not change unless significant changes are made to the illumination or imaging path of the instrument, in which case the entire normalization procedure should be repeated.

Since system A is the reference system, by definition, Gamma can be set to 1.0 and Offset can be set to 0.

For all remaining systems, the gamma and offset can be derived from the images of the normalization reference slide. Since there are minor variations of the images from each machine, due to scale factor differences or other image warping effects, an image pixel may not exactly overlay the same pixel as captured on another system. These are called sub-pixel registration errors. Therefore, it may not be possible to derive gamma and offset by direct comparison of individual pixel intensities from one system to the corresponding pixel from another system. Instead, in an embodiment, a statistical approach is employed which compares the intensity histograms for the two images captured on two different systems (e.g., the reference system and the system to be standardized).

The calculation of the image histograms requires that equivalent areas be identified in each image. A correlation-based method can be used, whereby a rectangular area in one of the images is chosen as the reference area. A search for an equivalent-sized target area in the second image is then made. For each candidate target area, the reference and target intensity values are compared for each pixel and the root-mean-squared (RMS) difference is calculated. The target area with the lowest RMS difference can be chosen as the target area to be used, along with the reference area, in the histogram calculations.

In an embodiment, a "histogram matching" method is used as the basis for determining gamma and offset of a system to be standardized from the histograms. In this method, the cumulative distribution function (CDF) for each image histogram is calculated. A mapping (gamma) is determined by finding the corresponding intensity in each image for which the cumulative frequencies match.

A drawback with using the gamma function directly is that it may not sample all of the intensity values which will be encountered for future images, so that some form of extrapolation is needed. Additionally, the gamma function can have a large number of degrees of freedom (equal to the number of histogram bins) which may introduce error in the details of the gamma function. In an embodiment, these drawbacks can be overcome by applying a linear regression to the gamma function which reduces the table of numbers from the gamma mapping to a straight line defined by slope and offset. The slope and offset are the $G_B$ and $O_B$ in equation (1) above.

Regression also provides an opportunity for estimating errors in the linear formula. For example, the RMS difference between the straight line and the gamma function is one method for estimating the standard error in linear prediction. Visual comparison of the regression line to the gamma function can also reveal any nonlinear bias that may exist between machines.

Upon completion of step (3), each system will have been normalized with respect to the reference system, and the initial drift reference of each system will have been determined.

Step (4) Creating Standardized Images:

Depending on the accuracy requirements of the user and the drift characteristics of the imaging system, a "Drift Correction" should be performed at regular intervals for each instrument. In many cases, this correction can be performed once per day, or prior to each use of the system. Using the colored plastic slide or other suitable "Drift Slide" from step (1), a drift correction image is captured. The drift correction for a system at time t, D(t), is calculated per the following equation (6):

$$d(t) = \text{average pixel intensity/exposure} \qquad \text{equation (6)}$$

Once D(t) has been obtained, the system can be used to capture an image of any specimen having the same characteristics as used in the normalization carried out in step (2).

Equation (4) may be used to correct the pixel intensities saved in the image file, or alternately, the image may be saved unaltered, allowing image analysis or viewing software to correct pixel intensities as the pixel values are retrieved. Since the resulting image correction can possibly increase the apparent intensity beyond what the image format allows, this method has the benefit of maintaining the best signal-to-noise ratio while avoiding pixel value "overflow" which appears as saturation, although the original image pixels were not saturated.

Benefits of this Approach

In addition to the obvious benefits derived from standardization of two or more systems, this approach also allows for recovery after loss of calibration slides, or damage or intentional modifications to any system. It also supports new systems being added to the standardized set. Once a group of machines have been standardized, the original reference system is no longer necessary for future standardizations because any standardized system can later be used as a substitute for the original reference machine. This allows standardization of a machine by comparing the machine to a (virtual) reference machine, thereby referencing back to the original system.

In one embodiment, a reference machine can be chosen at the factory and a number of standardized machines can be maintained so that any other machine can always be re-standardized at any point in time in order to maintain the performance of all machines at all sites within some desired tolerance.

Example Scanning Instruments

At this point it should be noted that although the various scanning instruments described herein use line scan cameras to image the sample data, any type of scanning system that creates a digital image of the sample is suitable for use with the present systems and methods for standardizing fluorescence microscopy systems.

Turning now to a description of example scanning instruments that could be used with the present standardization technique, FIG. 1 illustrates a block diagram of an embodiment of an optical microscopy system 10. The heart of the system 10 is a microscope slide scanner 11 that serves to scan and digitize a specimen or sample 12. The sample 12 can be anything that may be interrogated by optical microscopy. For instance, the sample 12 may be a microscope slide or other sample type that may be interrogated by optical microscopy. A microscope slide is frequently used as a viewing substrate for specimens that include tissues and cells, chromosomes, DNA, protein, blood, bone marrow, urine, bacteria, beads, biopsy materials, or any other type of biological material or substance that is either dead or alive, stained or unstained (e.g. using flourochromes), labeled or unlabeled. The sample 12 may also be an array of any type of DNA or DNA-related material such as cDNA or RNA or protein that is deposited on any type of slide or other substrate, including any and all samples commonly known as microarrays. The sample 12 may be a microtiter plate, for example a 96-well plate. Other examples of the sample 12 include integrated circuit boards, electrophoresis records, petri dishes, film, semiconductor materials, forensic materials, or machined parts.

The scanner 11 includes a motorized stage 14, a microscope objective lens 16, a line scan camera 18, and a data processor 20. The sample 12 is positioned on the motorized stage 14 for scanning. The motorized stage 14 is connected to a stage controller 22 which is connected in turn to the data processor 20. The data processor 20 determines the position of the sample 12 on the motorized stage 14 via the stage controller 22. In the presently preferred embodiment, the motorized stage 14 moves the sample 12 in at least the two axes (x/y) that are in the plane of the sample 12. Fine movements of the sample 12 along the optical z-axis may also be necessary for certain applications of the scanner 11, for example, for focus control. Z-axis movement is preferably accomplished with a piezo positioner 24, such as the PIFOC from Polytec PI or the MIPOS 3 from Piezosystem Jena. The piezo positioner 24 is attached directly to the microscope objective 16 and is connected to and directed by the data processor 20 via a piezo controller 27. A means of providing a coarse focus adjustment may also be needed and can be provided by z-axis movement as part of the motorized stage 14 or a manual rack-and-pinion coarse focus adjustment (not shown).

In the presently preferred embodiment, the motorized stage 14 includes a high precision positioning table with ball bearing linear ways to provide smooth motion and excellent straight line and flatness accuracy. For example, the motorized stage 14 could include two Daedal model 106004 tables stacked one on top of the other. Other types of motorized stages 14 are also suitable for the scanner 11, including stacked single axis stages based on ways other than ball bearings, single- or multiple-axis positioning stages that are open in the center and are particularly suitable for trans-illumination from below the sample, or larger stages that can support a plurality of samples. In the presently preferred embodiment, motorized stage 14 includes two stacked single-axis positioning tables, each coupled to two millimeter leadscrews and Nema-23 stepping motors. At the maximum lead screw speed of twenty-five revolutions per second, the maximum speed of the sample 12 on the motorized stage 14 is fifty millimeters per second. Selection of a lead screw with larger diameter, for example five millimeters, can increase the maximum speed to more than 100 millimeters per second. The motorized stage 14 can be equipped with mechanical or optical position encoders which has the disadvantage of adding significant expense to the system. Consequently, the presently preferred embodiment does not include position encoders. However, if one were to use servo motors in place of stepping motors, then one should use position feedback for proper control.

Position commands from the data processor 20 are converted to motor current or voltage commands in the stage controller 22. In an embodiment, the stage controller 22 includes a 2-axis servo/stepper motor controller (Compumotor 6K2) and two 4-amp microstepping drives (Compumotor OEMZL4). Microstepping provides a means for commanding the stepper motor in much smaller increments than the relatively large single 1.8 degree motor step. For example, at a microstep of 100, the sample 12 can be commanded to move at steps as small as 0.1 micrometer. A microstep of 25,000 is used in an embodiment. Smaller step sizes are also possible. It should be obvious that the optimum selection of the motorized stage 14 and the stage controller 22 depends on many factors, including the nature of the sample 12, the desired time for sample digitization, and the desired resolution of the resulting digital image of the sample 12.

The microscope objective lens 16 can be any microscope objective lens commonly available. One of ordinary skill in the art will realize that the choice of which objective lens to use will depend on the particular circumstances. In an embodiment, the microscope objective lens 16 is of the infinity-corrected type.

The sample 12 is illuminated by an illumination system 28 that includes a light source 30 and illumination optics 32. The light source 30 in an embodiment includes a variable intensity halogen light source with a concave reflective mirror to maximize light output and a KG-1 filter to suppress heat. However, the light source 30 could also be any other type of arc-lamp, laser, or other source of light. The illumination optics 32 in an embodiment include a standard Köhler illumination system with two conjugate planes that are orthogonal to the optical axis. The illumination optics 32 are representative of the bright-field illumination optics that can be found on most commercially available compound microscopes sold by companies such as Carl Zeiss, Nikon, Olympus, or Leica. One set of conjugate planes includes (i) a field iris aperture illuminated by the light source 30, (ii) the object plane that is defined by the focal plane of the sample 12, and (iii) the plane containing the light-responsive elements of the line scan camera 18. A second conjugate plane includes (i) the filament of the bulb that is part of the light source 30, (ii) the aperture of a condenser iris that sits immediately before the condenser optics that are part of the illumination optics 32, and (iii) the back focal plane of the microscope objective lens 16. In an embodiment, the sample 12 is illuminated and imaged in transmission mode, with the line scan camera 18 sensing optical energy that is transmitted by the sample 12, or conversely, optical energy that is absorbed by the sample 12.

The scanner 11 is equally suitable for detecting optical energy that is reflected from the sample 12, in which case the light source 30, the illumination optics 32, and the microscope objective lens 16 must be selected based on compatibility with reflection imaging. One possible embodiment may therefore be illumination through a fiber optic bundle that is positioned above or at an angle to the sample 12. Other possibilities include excitation that is spectrally conditioned by a monochromator. If the microscope objective lens 16 is selected to be compatible with phase-contrast microscopy, then the incorporation of at least one phase stop in the condenser optics that are part of the illumination optics 32 will enable the scanner 11 to be used for phase contrast microscopy. To one of ordinary skill in the art, the modifications required for other types of microscopy such as differential interference contrast and confocal microscopy should be readily apparent. Overall, the scanner 11 is suitable, with appropriate but well-known modifications, for the interrogation of microscopic samples in any known mode of optical microscopy.

Between the microscope objective lens 16 and the line scan camera 18 are situated the line scan camera focusing optics 34 that focus the optical signal captured by the microscope objective lens 16 onto the light-responsive elements of the line scan camera 18. In a modern infinity-corrected microscope the focusing optics between the microscope objective lens and the eyepiece optics, or between the microscope objective lens and an external imaging port, consist of an optical element known as a tube lens that is part of a microscope's observation tube. Many times the tube lens consists of multiple optical elements to prevent the introduction of coma or astigmatism. One of the motivations for the relatively recent change from traditional finite tube length optics to infinity corrected optics was to increase the physical space in which the optical energy from the sample 12 is parallel, meaning that the focal point of this optical energy is at infinity. In this case, accessory elements like dichroic mirrors or filters can be inserted into the infinity space without changing the optical path magnification or introducing undesirable optical artifacts.

Infinity-corrected microscope objective lenses are typically inscribed with an infinity mark. The magnification of an infinity corrected microscope objective lens is given by the quotient of the focal length of the tube lens divided by the focal length of the objective lens. For example, a tube lens with a focal length of 180 millimeters will result in 20× magnification if an objective lens with 9 millimeter focal length is used. One of the reasons that the objective lenses manufactured by different microscope manufacturers are not compatible is because of a lack of standardization in the tube lens focal length. For example, a 20× objective lens from Olympus, a company that uses a 180 millimeter tube lens focal length, will not provide a 20× magnification on a Nikon microscope that is based on a different tube length focal length of 200 millimeters. Instead, the effective magnification of such an Olympus objective lens engraved with 20× and having a 9 millimeter focal length will be 22.2×, obtained by dividing the 200 millimeter tube lens focal length by the 9 millimeter focal length of the objective lens. Changing the tube lens on a conventional microscope is virtually impossible without disassembling the microscope. The tube lens is part of a critical fixed element of the microscope. Another contributing factor to the incompatibility between the objective lenses and microscopes manufactured by different manufacturers is the design of the eyepiece optics, the binoculars through which the specimen is observed. While most of the optical corrections have been designed into the microscope objective lens, most microscope users remain convinced that there is some benefit in matching one manufacturer's binocular optics with that same manufacturer's microscope objective lenses to achieve the best visual image.

The line scan camera focusing optics 34 include a tube lens optic mounted inside of a mechanical tube. Since the scanner 11, in its preferred embodiment, lacks binoculars or eyepieces for traditional visual observation, the problem suffered by conventional microscopes of potential incompatibility between objective lenses and binoculars is immediately eliminated. One of ordinary skill will similarly realize that the problem of achieving parfocality between the eyepieces of the microscope and a digital image on a display monitor is also eliminated by virtue of not having any eyepieces. Since the scanner 11 also overcomes the field of view limitation of a traditional microscope by providing a field of view that is practically limited only by the physical boundaries of the sample 12, the importance of magnification in an all-digital imaging microscope such as provided by the present scanner 11 is limited. Once a portion of the sample 12 has been digitized, it is straightforward to apply electronic magnification, sometimes known as electric zoom, to an image of the sample 12 in order to increase its magnification. Increasing the magnification of an image electronically has the effect of increasing the size of that image on the monitor that is used to display the image. If too much electronic zoom is applied, then the display monitor will be able to show only portions of the magnified image. It is not possible, however, to use electronic magnification to display information that was not present in the original optical signal that was digitized in the first place. Since one of the objectives of the scanner 11 is to provide high quality digital images, in lieu of visual observation through the eyepieces of a microscope, it is important that the content of the images acquired by the scanner 11 include as much image detail as possible. The term resolution is typically used to describe such image detail and the term diffraction-limited is used to describe the wavelength-limited maximum spatial detail available in an optical signal. The scanner 11 provides diffraction-limited digital imaging by selection of a tube lens focal length that is matched according to the well know Nyquist sampling criteria to both the size of an individual pixel element in a light-sensing camera such as the line scan camera 18 and to the numerical aperture of the microscope objective lens 16. It is well known that numerical aperture, not magnification, is the resolution-limiting attribute of a microscope objective lens 16.

An example will help to illustrate the optimum selection of a tube lens focal length that is part of the line scan camera focusing optics 34. Consider again the 20× microscope objective lens 16 with 9 millimeter focal length discussed previously and assume that this objective lens has a numerical aperture of 0.50. Assuming no appreciable degradation from the condenser, the diffraction-limited resolving power of this objective lens at a wavelength of 500 nanometers is approximately 0.6 micrometers, obtained using the well-known Abbe relationship. Assume further that the line scan camera 18, which in an embodiment has a plurality of 14 micrometer square pixels, is used to detect a portion of the sample 12. In accordance with sampling theory, it is necessary that at least two sensor pixels subtend the smallest resolvable spatial feature. In this case, the tube lens must be selected to achieve a magnification of 46.7, obtained by dividing 28 micrometers, which corresponds to two 14 micrometer pixels, by 0.6 micrometers, the smallest resolvable feature dimension. The optimum tube lens optic focal length is therefore about 420 millimeters, obtained by multiplying 46.7 by 9. The line scan focusing optics 34 with a tube lens optic having a focal length of 420 millimeters will therefore be capable of acquiring images with the best possible spatial resolution, similar to what would be observed by viewing a specimen under a microscope using the same 20× objective lens. To reiterate, the scanner 11 utilizes a traditional 20× microscope objective lens 16 in a higher magnification optical configuration, in this example about 47×, in order to acquire diffraction-limited digital images. If a traditional 20× magnification objective lens 16 with a higher numerical aperture were used, say 0.75, the required tube lens optic magnification for diffraction-limited imaging would be about 615 millimeters, corresponding to an overall optical magnification of 68×. Similarly, if the numerical aperture of the 20× objective lens were only 0.3, the optimum tube lens optic magnification would only be about 28×, which corresponds to a tube lens optic focal length of approximately 252 millimeters. The line scan camera focusing optics 34 may be modular elements of the scanner 11 which can be interchanged as necessary for optimum digital imaging. The advantage of diffraction-limited digital imaging is particularly significant for applications, for example bright field microscopy, in which the reduction in signal brightness that accompanies increases in magnification is readily compensated by increasing the intensity of an appropriately designed illumination system 28.

In principle, it is possible to attach external magnification-increasing optics to a conventional microscope-based digital imaging system to effectively increase the tube lens magnification so as to achieve diffraction-limited imaging as has just been described for the present scanner 11. However, the resulting decrease in the field of view is often unacceptable, making this approach impractical. Furthermore, many users of microscopes typically do not understand enough about the details of diffraction-limited imaging to effectively employ these techniques on their own. In practice, digital cameras are attached to microscope ports with magnification-decreasing optical couplers to attempt to increase the size of the field of view to something more similar to what can be seen through the eyepiece. The standard practice of adding de-magnifying optics is a step in the wrong direction if the goal is to obtain diffraction-limited digital images.

In a conventional microscope, different power objectives lenses are typically used to view the specimen at different resolutions and magnifications. Standard microscopes have a nosepiece that holds five objectives lenses. In an all-digital imaging system, such as the present scanner 11, there is a need for only one microscope objective lens 16 with a numerical aperture corresponding to the highest spatial resolution desirable. An embodiment of the scanner 11 provides for only one microscope objective lens 16. Once a diffraction-limited digital image has been captured at this resolution, it is straightforward using standard digital image processing techniques, to present imagery information at any desirable reduced resolutions and magnifications.

In an embodiment, the scanner 11 is based on a Dalsa SPARK line scan camera 18 with 1024 pixels (picture elements) arranged in a linear array, with each pixel having a dimension of 14 by 14 micrometers. Any other type of linear array, whether packaged as part of a camera or custom-integrated into an imaging electronic module, can also be used. The linear array in the an embodiment effectively provides eight bits of quantization, but other arrays providing higher or lower level of quantization may also be used. Alternate arrays based on 3-channel red-green-blue (RGB) color information or time delay integration (TDI), may also be used. TDI arrays provide a substantially better signal-to-noise ratio (SNR) in the output signal by summing intensity data from previously imaged regions of a specimen, yielding an increase in the SNR that is in proportion to the square-root of the number of integration stages. TDI arrays can comprise multiple stages of linear arrays. TDI arrays are available with 24, 32, 48, 64, 96, or even more stages. The scanner 11 can also support linear arrays that are manufactured in a variety of formats including some with 512 pixels, some with 1024 pixels, and others having as many as 4096 pixels. Appropriate, but well known, modifications to the illumination system 28 and the line scan camera focusing optics 34 may be required to accommodate larger arrays. Linear arrays with a variety of pixel sizes can also be used in scanner 11. The salient requirement for the selection of any type of line scan camera 18 is that the sample 12 can be in motion with respect to the line scan camera 18 during the digitization of the sample 12 in order to obtain high quality images, overcoming the static requirements of the conventional imaging tiling approaches known in the prior art.

The output signal of the line scan camera 18 is connected to the data processor 20. The data processor 20 in an embodiment includes a central processing unit with ancillary electronics, for example a motherboard, to support at least one signal digitizing electronics board such as an imaging board or a frame grabber. In an embodiment, the imaging board is an EPIX PIXCID24 PCI bus imaging board. However, there are many other types of imaging boards or frame grabbers from a variety of manufacturers which could be used in place of the EPIX board. An alternate embodiment could be a line scan camera that uses an interface such as IEEE 1394, also known as Firewire, to bypass the imaging board altogether and store data directly on a data storage 38, such as a hard disk.

The data processor 20 is also connected to a memory 36, such as random access memory (RAM), for the short-term storage of data, and to the data storage 38, such as a hard drive, for long-term data storage. Further, the data processor 20 is connected to a communications port 40 that is connected to a network 42 such as a local area network (LAN), a wide area network (WAN), a metropolitan area network (MAN), an intranet, an extranet, or the global Internet. The memory 36 and the data storage 38 are also connected to each other. The data processor 20 is also capable of executing computer programs, in the form of software, to control critical elements of the scanner 11 such as the line scan camera 18 and the stage controller 22, or for a variety of image-processing functions, image-analysis functions, or networking. The data processor 20 can be based on any operating system, including operating systems such as Windows, Linux, OS/2, Mac OS, and Unix. In the presently preferred embodiment, the data processor 20 operates based on the Windows NT operating system.

The data processor 20, memory 36, data storage 38, and communication port 40 are each elements that can be found in a conventional computer. One example would be a personal computer such as a Dell Dimension XPS T500 that features a Pentium III 500 MHz processor and up to 756 megabytes (MB) of RAM. In the presently preferred embodiment, the computer, elements which include the data processor 20, memory 36, data storage 38, and communications port 40 are all internal to the scanner 11, so that the only connection of the scanner 11 to the other elements of the system 10 is the communication port 40. In an alternate embodiment of the scanner 11, the computer elements would be external to the scanner 11 with a corresponding connection between the computer elements and the scanner 11.

The scanner 11, in the presently preferred embodiment of the invention, integrates optical microscopy, digital imaging, motorized sample positioning, computing, and network-based communications into a single-enclosure unit. An advantage of packaging the scanner 11 as a single-enclosure unit with the communications port 40 as the primary means of data input and output are reduced complexity and increased reliability. The various elements of the scanner 11 are optimized to work together, in sharp contrast to traditional microscope-based imaging systems in which the microscope, light source, motorized stage, camera, and computer are typically provided by different vendors and require substantial integration and maintenance.

The communication port 40 provides a means for rapid communications with the other elements of the system 10, including the network 42. An example communications protocol for the communications port 40 is a carrier-sense multiple-access collision detection protocol such as Ethernet, together with the TCP/IP protocol for transmission control and internetworking. The scanner 11 is intended to work with any type of transmission media, including broadband, baseband, coaxial cable, twisted pair, fiber optics, DSL, or wireless.

In an embodiment, control of the scanner 11 and review of the imagery data captured by the scanner 11 are performed on a computer 44 that is connected to the network 42. The computer 44, in its presently preferred embodiment, is connected to a display monitor 46 to provide imagery information to an operator. A plurality of computers 44 may be connected to the network 42. In an embodiment, the computer 44 communicates with the scanner 11 using a network browser such as Internet Explorer from Microsoft or Netscape Communicator from AOL. Images can be stored on the scanner 11 in a common compressed format such a JPEG which is an image format that is compatible with standard image-decompression methods that are already built into most commercial browsers. Other standard or non-standard, lossy or lossless, image compression formats will also work. In the presently preferred embodiment, the scanner 11 is a web server providing an operator interface that is based on web pages that are sent from the scanner 11 to the computer 44. For dynamic review of imagery data, an embodiment of the scanner 11 is based on playing back, for review on the display monitor 46 that is connected to the computer 44, multiple frames of imagery data using standard multiple-frame browser compatible software packages such as Media-Player from Microsoft, Quicktime from Apple Computer, or RealPlayer from Real Networks. In the presently preferred embodiment, the browser on the computer 44 uses the hypertext transmission protocol (HTTP) together with TCP for transmission control.

There are, and will be in the future, many different means and protocols by which the scanner 11 could communicate with the computer 44, or a plurality of computers. While the some embodiments are based on standard means and protocols, the approach of developing one or multiple customized software modules known as applets is equally feasible and may be desirable for selected future applications of the scanner 11. Further, there are no constraints that computer 44 be of any specific type such as a personal computer (PC) or be manufactured by any specific company such as Dell. One of the advantages of a standardized communications port 40 is that any type of computer 44 operating common network browser software can communicate with the scanner 11.

If one so desires, it is possible, with some modifications to the scanner 11, to obtain spectrally resolved images. Spectrally resolved images are images in which spectral information is measured at every image pixel. Spectrally resolved images could be obtained by replacing the line scan camera 18 of the scanner 11 with an optical slit and an imaging spectrograph. The imaging spectrograph uses a two-dimensional CCD detector to capture wavelength-specific intensity data for a column of image pixels by using a prism or grating to disperse the optical signal that is focused on the optical slit along each of the rows of the detector.

Figure 2:
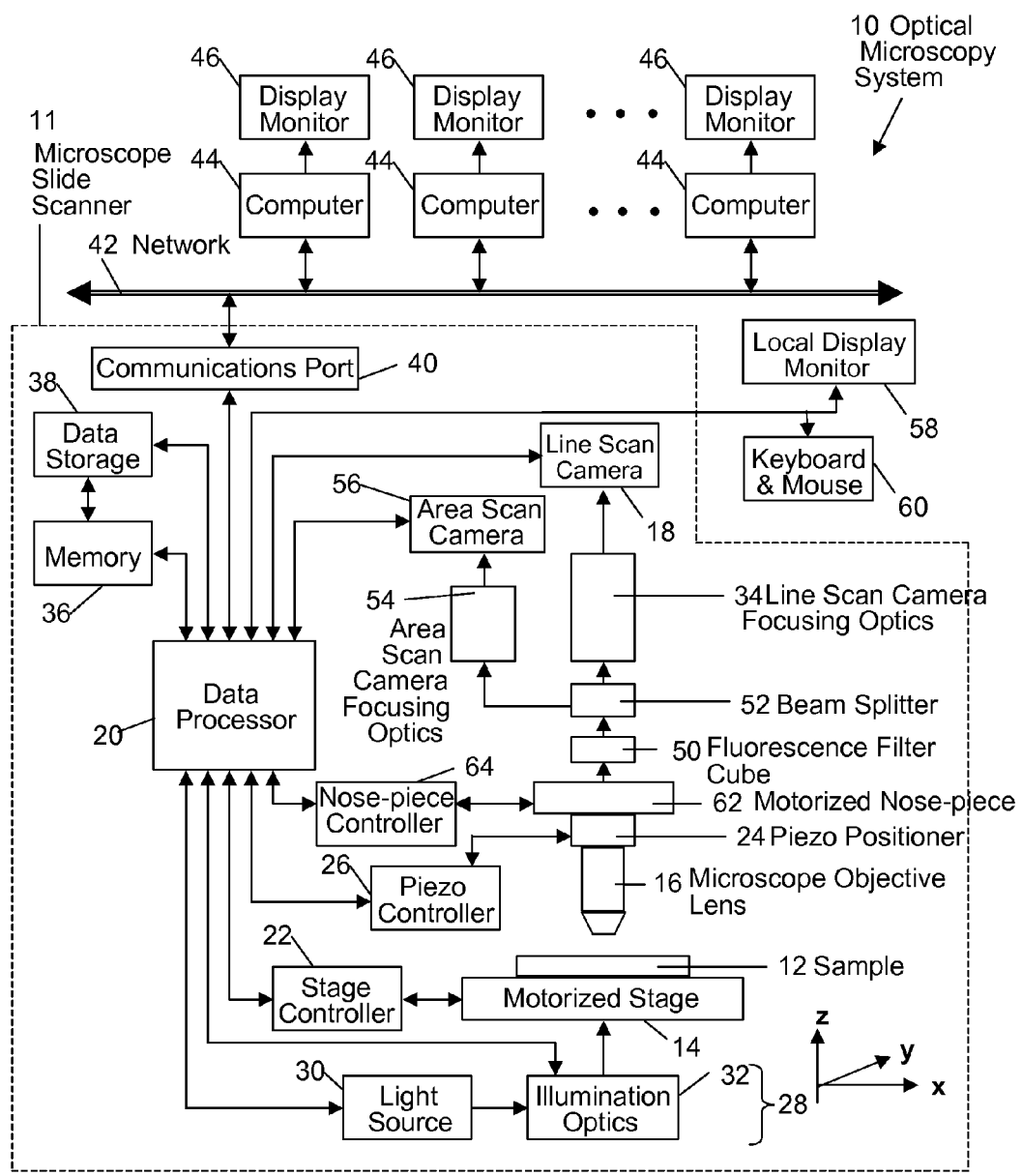
FIG. 2 is a block diagram of a second embodiment of an optical microscopy system according to an embodiment.

FIG. 2 illustrates a block diagram of a second embodiment of an optical microscopy system 10, according to an embodiment. In this system 10, the scanner 11 is more complex and expensive than the embodiment shown in FIG. 1. The additional attributes of the scanner 11 that are shown do not all have to be present for any alternate embodiment to function correctly. FIG. 2 is intended to provide a reasonable example of additional features and capabilities that could be incorporated into the scanner 11.

The alternate embodiment of FIG. 2 can provide for a much greater level of automation than the presently preferred embodiment of FIG. 1. A more complete level of automation of the illumination system 28 is achieved by connections between the data processor 20 and both the light source 30 and the illumination optics 32 of the illumination system 28. The connection to the light source 30 may control the voltage, or current, in an open or closed loop fashion, in order to control the intensity of the light source 30. Recall that the light source 30 is a halogen bulb in the presently preferred embodiment. The connection between the data processor 20 and the illumination optics 32 could provide closed loop control of the field iris aperture and the condenser iris to provide a means for ensuring that optimum Köhler illumination is maintained.

Use of the scanner 11 for fluorescence imaging requires easily recognized modifications to the light source 30, the illumination optics 32, and the microscope objective lens 16. The second embodiment of FIG. 2 also provides for a fluorescence filter cube 50 that includes an excitation filter, a dichroic filter, and a barrier filter. The fluorescence filter cube 50 is positioned in the infinity corrected beam path that exists between the microscope objective lens 16 and line scan camera focusing optics 34. One embodiment for fluorescence imaging could include the addition of a filter wheel or tunable filter into the illumination optics 32 to provide appropriate spectral excitation for the variety of fluorescent dyes or nanocrystals available on the market.

The addition of at least one beam splitter 52 into the imaging path allows the optical signal to be split into at least two paths. The primary path is via the line scan camera focusing optics 34, as discussed previously, to enable diffraction-limited imaging by the line scan camera 18. A second path is provided via an area scan camera focusing optics 54 for imaging by an area scan camera 56. It should be readily apparent that proper selection of these two focusing optics can ensure diffraction-limited imaging by the two camera sensors having different pixel sizes. The area scan camera 56 can be one of many types that are currently available, including a simple color video camera, a high performance, cooled, CCD camera, or a variable integration-time fast frame camera. The area scan camera 56 provides a traditional imaging system configuration for the scanner 11. The area scan camera 56 is connected to the data processor 20. If two cameras are used, for example the line scan camera 18 and the area scan camera 56, both camera types could be connected to the data processor using either a single dual-purpose imaging board, two different imaging boards, or the IEEE1394 Firewire interface, in which case one or both imaging boards may not be needed. Other related methods of interfacing imaging sensors to the data processor 20 are also available.

While the primary interface of the scanner 11 to the computer 44 is via the network 42, there may be instances, for example a failure of the network 42, where it is beneficial to be able to connect the scanner 11 directly to a local output device such as a display monitor 58 and to also provide local input devices such as a keyboard and mouse 60 that are connected directly to the data processor 20 of the scanner 11. In this instance, the appropriate driver software and hardware should be provided as well.

The second embodiment shown in FIG. 2 can also provide for a much greater level of automated imaging performance. Enhanced automation of the imaging of the scanner 11 can be achieved by closing the focus control loop comprising the piezo positioner 24, the piezo controller 26, and the data processor 20 using well-known methods of autofocus. The second embodiment also provides for a motorized nose-piece 62 to accommodate several objectives lenses. The motorized nose-piece 62 is connected to and directed by the data processor 20 through a nose-piece controller 64.

There are other features and capabilities of the scanner 11 which could be incorporated. For example, the process of scanning (i.e., moving) the sample 12 with respect to the microscope objective lens 16 that is substantially stationary in the x/y plane of the sample 12 could be modified to comprise scanning (i.e., moving) the microscope objective lens 16 with respect to a stationary sample 12. Scanning the sample 12, or scanning the microscope objective lens 16, or scanning both the sample 12 and the microscope objective lens 16 simultaneously, are possible embodiments of the scanner 11 which can provide the same large contiguous digital image of the sample 12 as discussed previously.

The scanner 11 also provides a general purpose platform for automating many types of microscope-based analyses. The illumination system 28 could be modified from a traditional halogen lamp or arc-lamp to a laser-based illumination system to permit scanning of the sample 12 with laser excitation. Modifications, including the incorporation of a photomultiplier tube or other non-imaging detector, in addition to or in lieu of the line scan camera 18 or the area scan camera 56, could be used to provide a means of detecting the optical signal resulting from the interaction of the laser energy with the sample 12.

Figure 3:
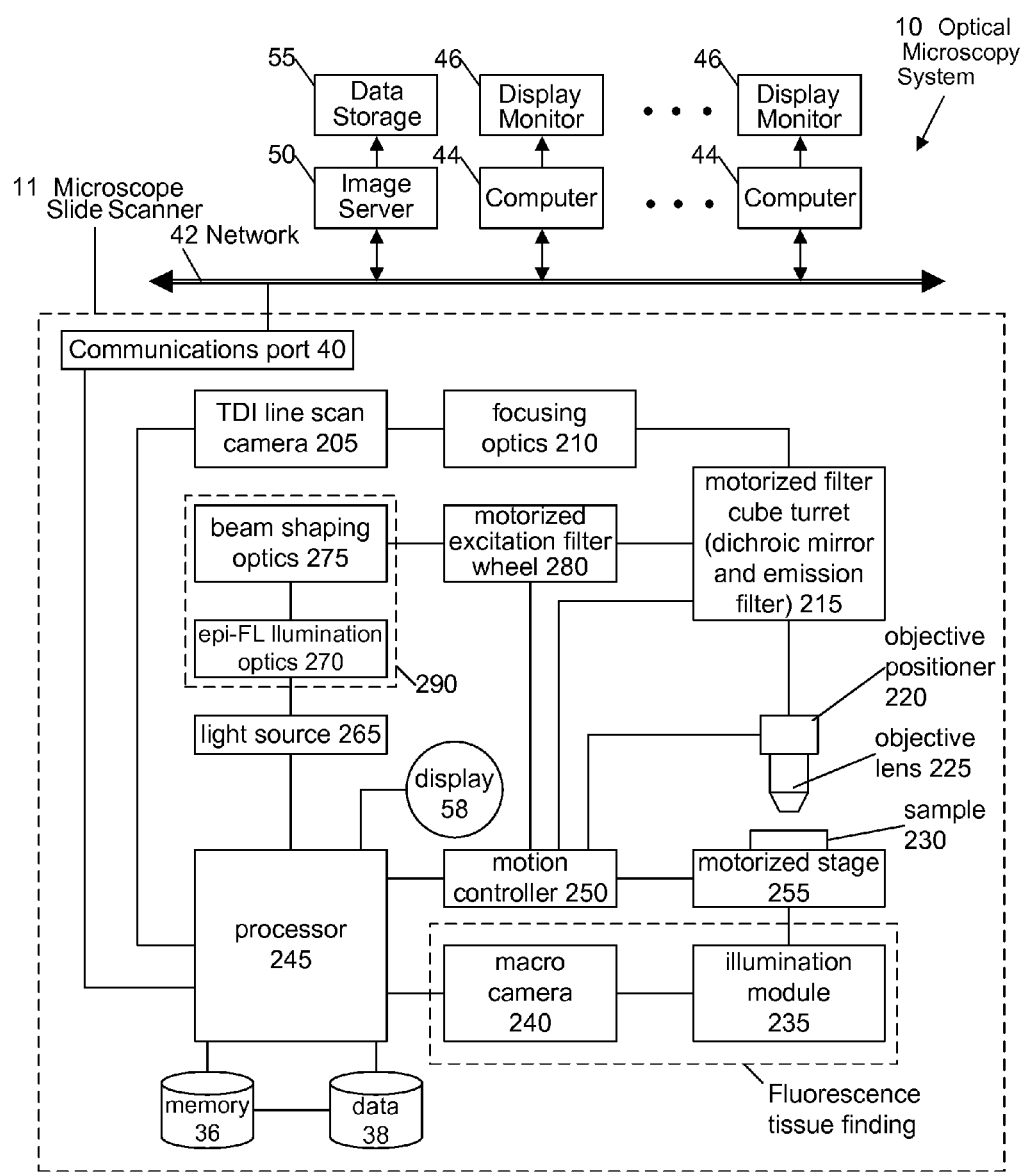
FIG. 3 is a block diagram of a third embodiment of an optical microscopy system according to an embodiment.

FIG. 3 is a block diagram of a third embodiment of an optical microscopy system 10 according to an embodiment. In the illustrated embodiment, the fluorescence scanner system 11 comprises a processor 245 that is communicatively coupled with a data storage area 38 that can include, e.g., volatile and persistent computer readable storage mediums. The processor 245 executes programmed modules in memory 36 and/or data storage 38 to control the macro camera 240, TDI line scan camera 205, focusing optics 210, motorized filter cube turret 215, and objective positioner 220 that is coupled to the objective lens 225. The processor also executes programmed modules to control the illumination module 235, motion controller 250 and motorized stage 255 that supports the sample 230. The processor also executes programmed modules to control the light source 265, the optimized epifluorescence illumination module 290 that comprises the epifluorescence illumination optics 270 and the optional beam shaping optics 275, and the motorized excitation filter wheel 280.

In operation, the various components of the fluorescence scanner system 11 and the programmed modules stored in memory 36 and/or data storage 38 enable automatic scanning and digitizing of the fluorescence sample 230. Microscope slides (not shown) are often used as a platform to support the fluorescence sample 230 and can be securely placed on the motorized stage 255 of the fluorescence scanner system 11 for scanning the sample 230. Under control of the processor 245, the motorized stage 255 accelerates the sample 230 to a substantially constant velocity for sensing by the TDI line scan camera 205, where the speed of the stage is synchronized with the line rate of the TDI line scan camera 205. After scanning of a stripe of image data, the motorized stage 255 decelerates and brings the sample 230 to a substantially complete stop before additional scanning of the same stripe or a different stripe.

The sample 230 can be any type of specimen that has been labeled with florescence dyes or fluorochrome, for example, tissue, cells, DNA and protein are types of samples, just to name a few. The fluorescence sample 230 can also be an array of specimen, for example, tissue sections, DNA, or DNA related material deposited on a substrate. As will be understood by those skilled in the art, any fluorescence specimen that can be interrogated by a fluorescence optical microscope can also be scanned by the fluorescence scanner system 11 to create a digital slide image of the fluorescence sample 230.

Fluorescence molecules are photon sensitive molecules that can absorb light at a specific wavelength (excitation). These photon sensitive molecules also emit light at a higher wavelength (emission). Because the efficiency of this photoluminescence phenomenon is very low, the amount of emitted light is often very low. The low amount of emitted light frustrates conventional techniques for scanning and digitizing the sample 230. Advantageously, use of the TDI line scan camera 205 that includes multiple linear sensor arrays increases the sensitivity of the camera by exposing the same area of the sample 230 to the multiple linear sensor arrays of the TDI line scan camera 205. This is particularly useful when scanning faint fluorescence samples with low emitted light. In alternative embodiments, the TDI line scan camera 205 may include 64, 96 or 120 linear sensor arrays, which may be charge coupled device ("CCD") arrays.

In one embodiment, the TDI line scan camera 205 is a monochrome TDI line scan camera, although the systems and methods described herein are not limited to monochrome cameras. Advantageously, monochrome images are ideal in fluorescence microscopy because they provide a more accurate representation of the actual signals from the various channels present on the sample. As will be understood by those skilled in the art, a fluorescence sample 230 can be labeled with multiple florescence dyes that emit light at different wavelengths, which are also referred to as "channels."

Furthermore, because the low and high end signal levels of various fluorescence samples present a wide spectrum of wavelengths for the TDI line scan camera 205 to sense, it is desirable for the low and high end signal levels that the TDI line scan camera 205 can sense to be similarly wide. Accordingly, in one embodiment a TDI line scan camera 205 used in the fluorescence scanning system 11 is a monochrome 10-bit 64 stage TDI line scan camera. It should be noted that a variety of bit depths for the TDI line scan camera 205 can be employed for use with the fluorescence scanning system 11.

In one embodiment, the fluorescence scanning system 11 uses a high precision and tightly coordinated XY grid to aid in the location of the sample 230 on the motorized stage 255. In one embodiment, the motorized stage 255 is a linear motor based XY stage with high precision encoders employed on both the X and the Y axis. For example, a 50 nanometer encoder can be used on the axis in the scanning direction and a 5 nanometer encoder can be used on the axis that is in the direction perpendicular to the scanning direction and on the same plane. Objective lens 225 is also mounted on the objective positioner 220 which employs a linear motor on the optical axis with a 50 nanometer encoder. In one embodiment, the three XYZ axes are coordinated and controlled in a closed loop manner using motion controller 250 that includes a motion control drive (not shown) and a motion control board (not shown). Control and coordination is maintained by processor 245 that employs memory a36 and/or data storage area 38 for storing information and instructions, including the computer executable programmed steps for scanning system 11 operation.

In one embodiment, the objective lens 225 is a plan APO infinity corrected objective that is suitable for fluorescence microscopy (e.g., an Olympus 20×, 0.75 NA). Advantageously, objective lens 225 is capable of correcting for chromatic and spherical aberrations. Because objective lens 225 is infinity corrected, other optical components such as filters, magnification changer lenses, etc. can be placed in the optical path above the objective lens 225 where the light beam passing through the objective lens becomes a collimated light beam. The objective lens 255 combined with focusing optics 210 provides the total magnification for the fluorescence scanning system 11 and also provides for focusing on the surface of TDI line scan camera 205. The focusing optics 210 contain a tube lens and an optional 2× magnification changer. In one embodiment, the 2× magnification changer can allow objective lens 255 that is natively 20× to scan a sample 230 at 40× magnification.

For the scanning system 11 to effectively perform fluorescence microscopy, a suitable light source 265 needs to be employed. In alternative embodiments, arc lamps such as mercury, metal halide, xenon lamps or LED light sources can be used for this purpose. In one embodiment, light source 265 is an arc based light source such as a 200 watt mercury based DC operated and processor controlled light source. Advantageously, the light source 265 allows the processor 245 to manage shutter control and iris control. In one embodiment, a liquid light guide (not shown) can be used to deliver light to the field of view of the objective lens 225, where scanning takes place, or to other desirable locations within the fluorescence scanning system 11. For example, a 3 mm core liquid light guide can be used to deliver light.

The fluorescence scanning system 11 additionally includes illumination optics that include epifluorescence illumination optics 270 and optional beam shaping optics 275 that collectively are shown as optimized epifluorescence illumination 290. The epifluorescence illumination optics 270 condenses the excitation light on the sample 230 through the objective lens 225. As is the case in epifluorescence illumination, the emitted light from the sample is also collected with the same objective lens 225. One particular advantage of using epifluorescence illumination is to maximize the blockage of excitation light reaching the multiple linear array sensors of the TDI line scan camera 205. In turn, this also maximizes the amount of emitted light that reaches the multiple linear array sensors of the TDI line scan camera 205.

The epifluorescence illumination optics 270 can be implemented using Dichroic mirrors that provide wavelength dependent reflectivity and transmission. As a result, the excitation light gets reflected off the surface of a Dichroic mirror and is guided through the objective lens 225 to reach the sample 230. However, the emitted light from the sample 230, which is at a higher wavelength, will pass through the Dichroic mirror and reach the multiple linear array sensors of the TDI line scan camera 205.

The epifluorescence illumination optics 270 also collimates the light from the light source 265. In alternative embodiments, this is accomplished using Kohler or Critical illumination. Kohler illumination provides the most uniform light illumination on the sample 230 to minimize shading in digital slide images while Critical illumination provides the maximum light intensity on the sample to decrease the necessary imaging exposure time. Both Kohler and Critical illumination can be employed by the fluorescence scanning system 11.

In one embodiment, the epifluorescence illumination optics 270 include relay lens tube optics (not shown) that are designed to collimate the light received from light source 265 through a liquid light guide (not shown) and deliver the light to the sample 230. In this embodiment, the light profile on the sample has minimal roll off within the imaging view through the objective lens 225.

In an alternative embodiment, the optional beam shaping optics 275 operate to illuminate just the portion of the sample 235 that is being sensed by the multiple linear array sensors of the TDI line scan camera 205. Advantageously, the beam shaping optics 275 reshape the illumination area from its natural circular shape into a thin oval shape that closely approximates the rectangular sensor area. The reshaped illumination area advantageously also receives increased light energy. Reshaping the illumination area is a vast improvement over conventional masking, which discards all of the light energy outside of the rectangular mask. Advantages of the optional beam shaping optics 275 include: (a) preserving the sample from redundant exposure to the excitation light and thereby minimizing photobleaching of the sample; and (b) increasing the light energy delivered to the illumination area on the sample and thereby allowing shorter exposure times (i.e., higher line rates) during scanning of the sample 230 to create a digital slide image. In combination, these two can provide a significant advantage.

The fluorescence scanning system 11 also includes motorized excitation filter wheel 280 that facilitates configuration and use of various filters. It is desirable to have certain filters available to increase the effectiveness of fluorescence microscopy. Some of the desirable filters include: (a) an excitation filter that narrows down the broad band light generated from the light source 265 to the specific band needed for excitation of the sample 230; (b) an emission filter to filter out excess light and possibly excitation light that may reach one or more of the linear array sensors of the TDI line scan camera 205; and (c) a Dichroic mirror as described above for use with epi-fluorescence illumination. Other filters can also be included.

In one embodiment, the fluorescence scanning system 11 includes a motorized wheel for excitation filters, a motorized wheel for emission filters, and a motorized wheel for Dichroic mirrors. Sliders can also be used in place of wheels. In an alternative embodiment, the fluorescence scanning system 11 includes a motorized excitation filter wheel 280 and a motorized filter cube turret 215 that includes the emission filter and the Dichroic mirrors. One particular advantage of separating the excitation filter(s) from the emission filter(s) and the dichroic mirrors is related to the use of a TDI line scan camera 205 that is monochrome. Specifically, use of a monochrome TDI line scan camera 205 causes each stripe region of the sample 230 to be scanned and digitized multiple times—once for each emission wavelength (i.e., channel) to be interrogated. Registration of the multiple scans of a single stripe is therefore critically important to allow integration of the multiple scans into a single image that includes information from each channel.

Additionally, because the motorized filter cube turret 215 includes an emission filter and the Dichroic mirrors, the motorized filter cube turret 215 can implement a filter configuration in which multiple band filter cubes (Dichroic mirrors and emission filters) and single band excitation filters are used in combination (called a "Pinkel" configuration). Use of the Pinkel configuration advantageously allows scanning and digitization of the sample 230 multiple times while changing only the excitation filter using the motorized excitation filter wheel 280. Consequently, no mechanical or optical registration issues will be observed between images of the same stripe on the sample because there is no moving component in the imaging path. This is a significant advantage of separating the excitation filter(s) from the emission filter(s) and Dichroic mirrors when using a line scan camera (such as TDI line scan camera 205) that scans the same area of the sample 230 multiple times and combines the resulting multiple images.

In one embodiment, motorized excitation filter wheel 280 is a six position wheel that can accommodate standard 25 mm filters. The motorized excitation filter wheel 280 is under the control of the processor 245. As will be understood by those skilled in the art, any standard fluorescence filter can be used. Preferably, hard coated filters are used with the scanning system 11 because they are more durable and are easy to clean.

In one embodiment, motorized filter cube turret 215 is also a six positioned turret that holds filter cubes, for example standard Olympus filter cubes can be used. The motorized filter cube turret 215 is under the control of the processor 245. Both the motorized excitation filter wheel 280 and the motorized filter cube turret 215 filter are automatically placed in the illumination path or imaging path under control of the processor 245 depending on the particular fluorochromes on the sample 230 and the available filters configured in the fluorescence scanning system 11.

One particular challenge when imaging fluorescence samples is recognizing the sample 230 on the microscope slide and determining the area to be scanned and digitized into a digital slide image. Moreover, fluorescence samples often times appear to be transparent, which amplifies this challenge because regular imaging of the fluorescence sample using regular lighting does not necessarily provide a means to recognize the specimen on the slide. Accordingly, illumination module 235 is configured to apply oblique illumination to the fluorescence sample 230. Macro camera 240 is configured to capture the image of the sample after it is illuminated with oblique lighting by the illumination module 235. Advantageously, the tissue in the resulting image has enough contrast to be recognizable.

In one embodiment, illumination module 235 uses a white LED module (not shown) integrated with a beam diffuser lens (also not shown) positioned at an angle to illuminate the sample 230 at an appropriate angle. In one embodiment, oblique illumination at an angle of 30 degrees is used (as measured with respect to the surface of the microscope slide). However, it should be understood that oblique illumination at any angle in the range of 0 degrees to 85 degrees can be used. A zero degree angle (e.g., illuminating the sample 230 through the thickness of the slide) can be accomplished using, for example, a linear fiber. In one embodiment, additional shrouding around the illumination module 235 is provided to better channel the oblique light hitting the surface of the sample 230. Shrouding around the macro camera 240 is also provided to increase the amount of reflected light off the sample 230 that is captured by the macro camera 240 while also minimizing the amount of illumination light that is captured by the macro camera 240.

The processor 245 may include one or more processor cores, as will be understood by those skilled in the art. Additional separate processors may also be provided to control particular components or perform particular functions. For example, additional processors may include an auxiliary processor to manage data input, an auxiliary processor to perform floating point mathematical operations, a special-purpose processor having an architecture suitable for fast execution of signal processing algorithms (e.g., digital signal processor), a slave processor subordinate to the main processor (e.g., back-end processor), an additional processor for controlling the TDI line scan camera 205, the stage 255, the objective lens 225 or a display (not shown). Such additional processors may be separate discrete processors or may be integrated with the processor 245.

The processor 245 is preferably electrically connected to the various components of the fluorescence scanning system 11 in order to provide control and coordination and overall management of the fluorescence scanning system 11. Alternatively, the processor 245 can be in wireless communication with one or more of the various components of the fluorescence scanning system 11.

The memory 36 and data storage area 38 provide storage of data and instructions for programs executing on the processor 245. The memory 36 and/or data storage area 38 can include volatile and persistent storage of the data and instructions and may include a random access memory, a read only memory, a hard disk drive, removable storage drive, and the like.

The scanning system 11 may also include a communication interface (not shown) that allows software and data to be transferred between the scanning system 11 and external devices that are directly connected (e.g., a printer) or external devices such as one or more operator or user stations 44, and an image server system 50 that are connected via the network 42.

In one embodiment, computer executable instructions (e.g., programmed modules and software) are stored in the memory 36 and/or data storage area 38 and, when executed, enable the scanning system 11 to perform the various functions described herein. In this description, the term "computer readable storage medium" is used to refer to any media used to store and provide computer executable instructions to the scanning system 11 for execution by the processor 245. Examples of these media include data storage area 38 and any removable or external storage medium (not shown) communicatively coupled with the scanning system 11 either directly or indirectly, for example via the network 60.

Figure 4:
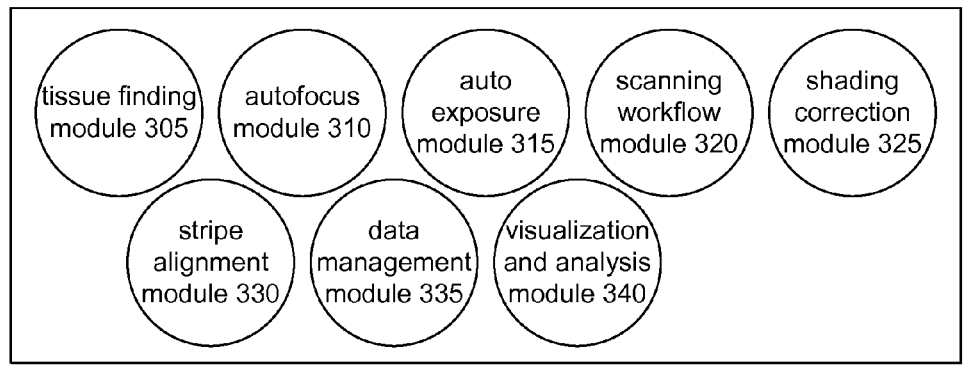
FIG. 4 is a block diagram illustrating an example set of modules in the scanner system of FIGS. 1-3, according to an embodiment.

FIG. 4 is a block diagram illustrating an example set of modules in the fluorescence scanner system 11 according to an embodiment of the invention. In the illustrated embodiment, the modules include the tissue finding module 305, autofocus module 310, auto exposure module 315, scanning workflow module 320, shading correction module 325, stripe alignment module 330, data management module 335, and the visualization and analysis module 340. In certain combinations, the various illustrated modules collaborate to perform whole slide fluorescence scanning. These modules may be stored, for example, in memory 36 and/or data storage 38, and executed by processors 20 or 245.

The tissue finding module 305 operates to determine the location of the sample 230 on the microscope slide. The location of the sample is determined with respect to the previously described XY coordinates for the motorized stage. The tissue finding module 305 analyzes image data from the macro camera 240 to determine the location of the tissue. Advantageously, oblique illumination of the sample 230 results in the macro camera 240 providing a high contrast image of the sample 230 to the tissue finding module 305. The tissue finding module 305 analyzes the high contrast image from the macro camera 240 to determine the location of the sample 230. For example, the highest contrast areas may define the perimeter of the specimen to allow the tissue finding algorithm 305 to determine an outline of the sample 230. In one embodiment, the tissue finding module 305 employs a thresholding algorithm which, given an image largely composed of black pixels (representing areas where there is no tissue present) and white pixels (representing areas where there is tissue present), calculates the minimum pixel intensity of a white pixel (the "threshold"). The threshold is then used to classify each pixel in the macro image as being tissue or not tissue. This chosen threshold minimizes the result of the following equation: $\omega_{nt}\sigma_{nt}+\omega_t\sigma_t$ where $\omega_{nt}$ is the probability that a pixel will be classified as not tissue, and $\sigma_{nt}$ is the variance of intensities of pixels classified as not tissue, and $\omega_t$ is the probability that a pixel will be classified as tissue, and $\sigma_t$ is the variance of intensities of pixels classified as tissue.

The autofocus module 310 operates to generate a focus map of the surface of the sample 230 so that the digital slide image that is created as a result of scanning the sample has optimal focus. The autofocus module 310 initially determines a set of points on the sample using the XY coordinates. Next, each point is visited by the TDI line scan camera, and the optimal focus height for the objective lens at each point is determined. In one embodiment, the optimal focus height for an XY point can be determined by scanning the XY point on the sample from the top end of the Z range of the objective to the bottom end of the Z range of the objective and then scanning the same point on the sample from the bottom end of the Z range of the objective to the top end of the Z range of the objective and then averaging the two. The height of the objective that provides the highest contrast in the scanned image data is then determined for both scans (i.e., top down and bottom up) and an average height is then calculated as the optimal focus height for that XY point.

In an alternative embodiment, the optimal focus height for an XY point can be determined by scanning the point on the sample from the top end of the Z range of the objective to the bottom end of the Z range of the objective, or vice versa. The height of the objective that provides the highest contrast in the scanned image data is then determined to be the optimal focus height for that XY point.

The result of either technique for determining the optimal focus height for an XY point is a set of focus points that each comprise an XY location and a focus height. The set of focus points is then used to calculate a non-planar focal surface that covers the scan area. The scan area can include the entire sample 230 or just a portion of the sample 230.

One particularly challenging aspect of determining the optimal focus height for an XY point on the sample 230 arises from the use of the TDI line scan camera 205. This is because the sensor in a TDI line scan camera comprises a plurality of linear sensing arrays (e.g., 64 or 96) located side by side in a uniformly spaced, parallel manner. During relative motion scanning, as the sample 230 moves perpendicular to the linear sensing arrays, the sample 230 is sensed by the first array, then the second array, and so on. Advantageously, this provides multiple exposures of each area of the sample 230 as it moves relative to the sensor. The multiple exposures are then combined to create the resulting image, which benefits from the increased exposure time without sacrificing the scanning speed. The increased exposure time is particularly useful when used for faint fluorescence samples, as explained above.

However, this advantage of the TDI line scan camera 205 becomes a liability when the perpendicular relative motion of the sample and the linear sensing arrays is removed, as is the case when determining the optimal focus height for an XY point on a sample. For example, as the TDI line scan camera 205 travels from the top end of its Z range to the bottom end of the Z range, each of the multiple linear sensing arrays captures image data for the portion of the sample 230 it can "see." As the TDI camera 205 successively integrates the image data from the various linear sensing arrays, the image data is not from the same exact portion of the sample 230. Accordingly, when the image data from the various linear sensing arrays are combined to create a resulting image, the resulting image appears blurred. This is referred to as spatial blurring.

A related problem with using the TDI line scan camera 205 is referred to as temporal blurring. In temporal blurring, the problem is that as the objective travels through its Z range, the first linear array sensor captures its image data at time t1. This image data is then integrated with the image data captured by the second linear array sensor at time t2, and so on. By the time the $96^{th}$ linear array sensor is capturing its image at t96, the Z level of the objective has changed sufficiently to be on a different focal plane. Thus, temporal blurring is also a challenge for identifying the optimal focus height for an XY point on the sample 230.

Accordingly, the autofocus module 310 operates such that for each XY focus point, the objective lens travels from the top end of its Z range to the bottom end of its Z range and then additionally travels back from the bottom end of its Z range to the top end of its Z range. The result of the top-to-bottom scan and the bottom-to-top scan are then averaged to determine the optimal focus height. This effectively eliminates the temporal blurring problems associated with using the TDI line scan camera 205 for identifying the optimal focus height at a focus point and allows the autofocus module 310 to use the average height of the objective that provides the most contrast in the top-to-bottom scanned image data and the bottom-to-top scanned image data as the optimal focus height for each XY point.

In an alternative embodiment, to eliminate problems associated with temporal blurring, during the top-to-bottom scan and during the bottom-to-top scan, the image data from each of the linear sensing arrays (e.g., from all 96 arrays) that is captured at each Z position is integrated into a single line of data. In this fashion, there would still be spatial blurring, but the temporal blurring is eliminated.

The autoexposure module 315 operates to determine the optimum exposure time for each of the fluorochromes on a sample being scanned by the fluorescence scanning system 40. The exposure time determination process typically uses a small area of the sample 230 that is representative of the overall sample 230 and the particular fluorochrome (i.e., the particular channel). The autoexposure module 315 obtains focused image data from a small area of the sample 230 and analyzes the image data to calculate an estimated optimal exposure time for the small area of the sample 230. The scan and analyze and calculate process is then repeated until the actual exposure time used by the TDI line scan camera 205 is substantially equal to the estimated optimal exposure time that is calculated.

Once the optimal exposure time has been calculated for one fluorochrome (i.e., channel) the autoexposure module 315 stores that exposure time in a data storage area for later use during the scan. The autoexposure module 315 then proceeds to determine the optimal exposure time for any remaining fluorochromes on the sample 230. Advantageously, the scanning system 11 employs a monochrome TDI line scan camera 205 and separate excitation and emission filter wheels, which allows the exposure time for each fluorochrome to be calculated independent of the other fluorochromes. This arrangement of the fluorescence scanning system 11 provides a significant advantage over fluorescence scanning systems that attempt to capture image data from multiple fluorochromes during one scanning movement.

The scanning workflow module 320 operates to manage the overall process for creating a digital slide image of a fluorescence sample 230 using the fluorescence scanning system 40. As previously described, the scanning system 11 uses a monochrome TDI line scan camera 205 with high sensitivity and high bit depth to achieve optimum imaging performance. However, fluorescence samples 230 are typically marked with multiple fluorochromes, which causes light to be emitted from the sample 230 in multiple wavelengths (i.e., channels). Accordingly, when scanning a multi-channel fluorescence sample 230, channel separation is achieved by the fluorescence scanning system 11 by the use of specialized filters. For maximum flexibility, the excitation filter is mounted separately from the emission filter, as described above. This allows for multiple filter combinations by means of a filter wheel having one or more excitation filters combined with a filter cube turret having one or more emission filter cubes. Since the filter wheel is a motor controlled device, to minimize scanning time, it is preferable to also minimize filter wheel rotations.

The scanning workflow module 320 can implement a very efficient process that advantageously minimizes the number of filter wheel rotations. For example, compared to a conventional image tiling system, the scanning workflow module 320 reduces the number of filter wheel rotations by a factor of 60 to 120. In a conventional image tiling system, for every small image tile, the filter wheel must be positioned "N" times, where N equals the number of channels. For a typical exposure time of 10 milliseconds per tile, significantly more time is spent rotating the filter wheel N times than is spent actually sensing the images. The fluorescence scanning system 40, in contrast, rotates the filter wheel only N times for each scanned stripe. Since a typical scanned image tile is roughly 1 megapixel, whereas a typical scanned stripe is roughly 60 megapixels, for each channel beyond the first, there is a 60 to 1 decrease in the number of filter wheel rotations due to the efficiency of the process implemented by the scanning workflow module 320.

The shading correction module 325 operates to correct for non-uniformity in the epifluorescence illumination optics and the TDI line scan camera 205. The shading correction module 325 scans a small area of the sample 320 (e.g., 1 mm) of the slide at a particular XY coordinate where no sample is present. In one embodiment, the scan is performed using predetermined focus parameters that were determined for the sample 320. The scan is performed at the maximum exposure time of the TDI line scan camera 205 in order to capture the light emitted by any residual dye present on the slide (background fluorescence). The average intensity for each pixel column in the scan is calculated and checked to ensure that an accurate illumination profile can be calculated, and then the shading correction module 325 calculates an illumination correction profile by comparing the average intensity of each pixel column to the maximum average intensity present in the image. This profile is calculated for each fluorochrome (i.e., channel) to be scanned by the fluorescence scanning system 40.

The stripe alignment module 330 operates to align adjacent stripes of image data that are captured by the TDI line scan camera 205. In one embodiment, the high precision XY accuracy of the motorized stage 255 allows each stripe of image data to be abutted against its adjacent neighbor in the resulting single file digital slide image. The high precision XY accuracy of the stage 255 therefore provides sufficiently aligned adjacent stripes without the need for any software implemented alignment that is dependent upon an analysis of the content of the image data. This solves a particular problem with respect to software based alignment of stripes of image data for fluorescence samples 230 that arises because fluorescence sample image data typically does not contain enough contrast in the overlap area of adjacent stripes to allow software based alignment of stripes of fluorescence sample image data.

In an alternative embodiment, the scanning system 11 uses software based alignment of stripes when there is sufficient contrast in the fluorescence sample image data. In this embodiment, the alignment of adjacent stripes is not determined based on a certain number of pixels determined to have the highest contrast in the overlap area of adjacent stripes. Instead, the stripe alignment module 330 calculates a contrast distribution of the entire overlap area of the adjacent stripes. The stripe alignment module 330 then identifies a contrast peak in the contrast distribution of the overlap area and defines a band around the contrast peak. The optimal stripe alignment is determined based on the pixels corresponding to the band around the contrast peak. Advantageously, oversaturated pixels are ignored when calculating the contrast distribution.

Additionally, for multi-channel fluorescence samples 230, optimal stripe alignment between adjacent stripes can be calculated for each channel and the channel providing the most robust alignment can be used. Advantageously, because the image data from the stripes corresponding to the various channels are combined in the digital slide image, alignment of only one channel between adjacent stripes is needed. Furthermore, the stripe alignment module 330 calculates stripe alignment in the direction perpendicular to the scanning direction one time. This can be calculated based on the high precision XY accuracy of the stage 255 in combination with the beginning of image data capture, which should be the same for all the channels.

The data management module 335 operates to manage the multi-channel image data generated by the TDI line scan camera 205 and related image data and metadata information. Initially, as with bright-field digital slide images, a fluorescence digital slide image scan can be stored in a single digital slide image file. If the sample 230 was scanned at multiple Z levels, the image for each of the various Z levels is also incorporated into the digital slide image file.

Additionally, because fluorescence scans typically include image data from multiple channels and each channel is related to the same sample 230, it is advantageous to store the multi-channel image data a single digital slide image file. Furthermore, it is also valuable to store related sub-imagery data and metadata related to instrument acquisition settings, image data descriptors, and sample information in the digital slide image file. Moreover, any known or scan-time computed inter-image relationships can also be stored in the digital slide image file.

Related sub-imagery may include an image of the slide label (e.g., a barcode), macro images of the whole slide, and a thumbnail of the acquired image. Metadata related to instrument acquisition settings may include exposure time, filter specifications, light source specifications, and calibration information. Metadata related to image data descriptors may include the intensity distribution of the image pixels, automatically determined regions of interest and regions of disinterest, image features such as contrast distribution, frequency distribution, texture, as well as figures of merit. Metadata related to sample information may include the tissue type and preparation as well as targeted biologic feature. Inter-image relationships include image translation and image rotation data.

In one embodiment, the fluorescence digital slide image file is structured and stored as a tiled, multi-layer image. The base layer is at the original scan resolution and subsequent layers are sub-sampled resolutions that form an image pyramid. Each layer is made up of one or more tiles and each tile of a layer can be compressed with a lossless or a lossy compression algorithm for improved disk and memory utilization, file transfer speeds and network image serving rates.

For multi-channel digital slide images, the base layer and each subsequent layer comprises the image data for each channel. For example, a four channel digital slide image would have a base layer divided into four quadrants where each quadrant included a complete image of the sample 230 at one of the four quadrants.

The digital slide images are stored in a data storage area, for example the data storage area 38 of the scanning system 11 or the data storage area 55 of an image server system 50 communicatively connected to scanning system 11 through network 42. In one embodiment, the data management module 335 itemizes each scanned image with respect to its associated patient, specimen, and slide, and may also record results of quantitative analysis in association with the stored digital slide image. The data management module 335 may also provide a user with access to all of the stored information as well as provide an interface to hospital and laboratory information systems for data sharing.

In an alternative embodiment, separate digital slide images can be created for each channel at which that the specimen 230 was scanned. In such an embodiment, a secondary file that references the related digital slide image files is created. The secondary file comprises the inter-image relationships as well as visualization preferences and adjustments (described below). This secondary file is called a fused image.

The visualization and analysis module 340 operates to facilitate viewing and analysis of a fluorescence digital slide image file. Each fluorescence digital slide image can be viewed at each of the various separate channels and/or viewed as a fused image where the image data from the various separate channels is overlayed into a single view of the sample that includes two or more channels. When the digital slide image is viewed (in separate or fused channels) the image of the entire sample 230 is available for real time image navigation, rotation, zooming, magnification and Z level depth traversal.

In one embodiment, the multiple fluorochrome channels may be viewed simultaneously by arranging them side by side or in a grid formation. Advantageously, the images are registered to enable synchronous navigation. For example, a four channel scan may be arranged in a four quadrant layout. In one embodiment, zooming one image causes all four quadrants to similarly zoom. Additionally, panning left on one quadrant, for example, pans left on all four quadrants, and so on.

Image viewing adjustments such as brightness, contrast, gamma, and false coloring are automatically determined using the stored image descriptors and the acquisition settings. In one embodiment, viewing adjustments can be made by a user at a user station 44 for the individual images and/or for a fused image (i.e., the combined image of two or more individual channel images). In addition, when viewing a fused image the relative translation and rotation corrections may be adjusted.

Interactive image exploration tools are also enabled by the digital visualization and analysis module 340 to instantly access fluorochrome responses on a cellular basis. Additionally, predetermined regions of interest may contain annotation that can be displayed to a user at the user station 44 to indicate meaningful biologic responses or to automatically quantitatively analyze. Additionally, the visualization and analysis module 340 may provide a user at the user station 44 with tools to annotate regions of interest and then store such annotations in the digital slide image file in relation to the base layer image. Advantageously, such annotations can be a useful to guide to document artifacts in an image, regions of interest in an image, or to identify a region of an image for reporting or quantitative analysis.

Additionally, the visualization and analysis module 340 may use predetermined or otherwise identified image features to locate similar image data or patterns using content based image retrieval techniques. Advantageously, this utility can provide a user at the user station 44 with related case information and image data.

In one embodiment, a client-server architecture permits a user at the user station 44 to view a fluorescence digital slide image located at the image server system 50 or the scanning system 11 by requesting the compressed image tiles at a specified pyramid level on an as needed basis and by performing client-side caching of tiles in anticipation of user requests.

The digital visualization and analysis module 340 additionally operates to facilitate whole slide quantitative analysis of the fluorescence digital slide images, whether the image is a quadrant style image or a fused style image. In one embodiment, the digital visualization and analysis module 340 can facilitate a quantitative analysis of a particular region of interest, instead of the entire digital slide image. Analysis results can be stored in a data storage area such as data storage areas 38, 55, or a data storage area of operator or user stations 44 for use with data management and reporting.

Figure 5:
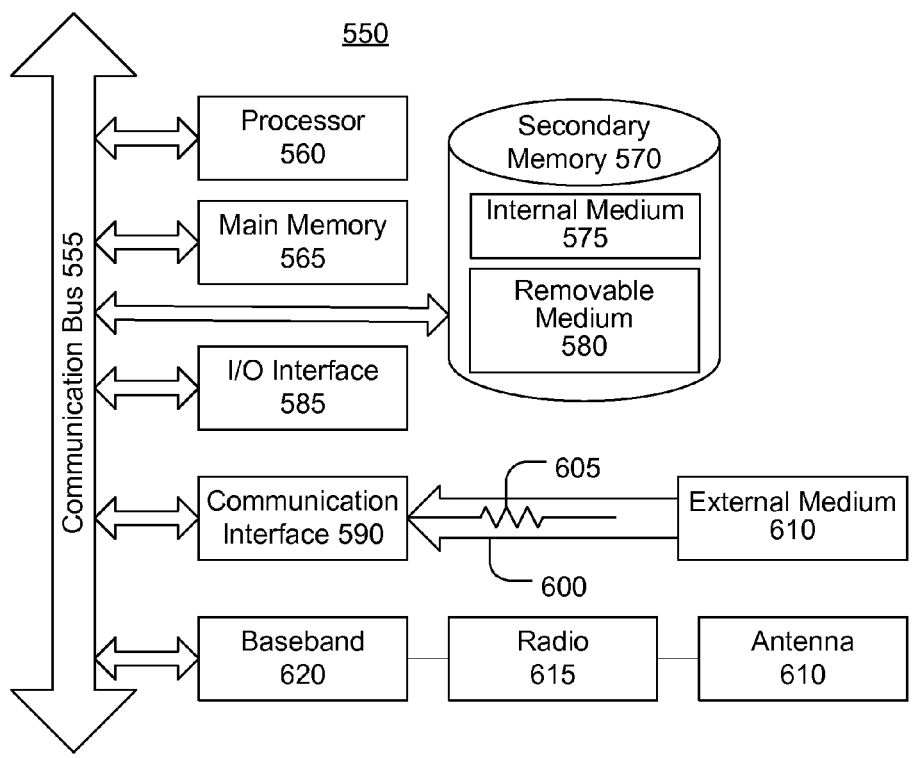
FIG. 5 is a block diagram illustrating an example wired or wireless processor-enabled system that may be used in connection with various embodiments described herein.

FIG. 5 is a block diagram illustrating an example wired or wireless processor enabled system that may be used in connection with various embodiments described herein. For example, the system 550 may be used in conjunction with the scanning devices illustrated in FIGS. 1-3. As will be clear to those skilled in the art, alternative processor enabled systems and/or architectures may also be used.

The system 550 preferably includes one or more processors, such as processor 560. Additional processors may be provided, such as an auxiliary processor to manage input/output, an auxiliary processor to perform floating point mathematical operations, a special-purpose microprocessor having an architecture suitable for fast execution of signal processing algorithms (e.g., digital signal processor), a slave processor subordinate to the main processing system (e.g., back-end processor), an additional microprocessor or controller for dual or multiple processor systems, or a coprocessor. Such auxiliary processors may be discrete processors or may be integrated with the processor 560.

The processor 560 is preferably connected to a communication bus 555. The communication bus 555 may include a data channel for facilitating information transfer between storage and other peripheral components of the system 550. The communication bus 555 further may provide a set of signals used for communication with the processor 560, including a data bus, address bus, and control bus (not shown). The communication bus 555 may comprise any standard or non-standard bus architecture such as, for example, bus architectures compliant with industry standard architecture ("ISA"), extended industry standard architecture ("EISA"), Micro Channel Architecture ("MCA"), peripheral component interconnect ("PCI") local bus, or standards promulgated by the Institute of Electrical and Electronics Engineers ("IEEE") including IEEE 488 general-purpose interface bus ("GPIB"), IEEE 696/S-100, and the like.

System 550 preferably includes a main memory 565 and may also include a secondary memory 570. The main memory 565 provides storage of instructions and data for programs executing on the processor 560. The main memory 565 is typically semiconductor-based memory such as dynamic random access memory ("DRAM") and/or static random access memory ("SRAM"). Other semiconductor-based memory types include, for example, synchronous dynamic random access memory ("SDRAM"), Rambus dynamic random access memory ("RDRAM"), ferroelectric random access memory ("FRAM"), and the like, including read only memory ("ROM").

The secondary memory 570 may optionally include a internal memory 575 and/or a removable medium 580, for example a floppy disk drive, a magnetic tape drive, a compact disc ("CD") drive, a digital versatile disc ("DVD") drive, etc. The removable medium 580 is read from and/or written to in a well-known manner. Removable storage medium 580 may be, for example, a floppy disk, magnetic tape, CD, DVD, SD card, etc.

The removable storage medium 580 is a non-transitory computer readable medium having stored thereon computer executable code (i.e., software) and/or data. The computer software or data stored on the removable storage medium 580 is read into the system 550 for execution by the processor 560.

In alternative embodiments, secondary memory 570 may include other similar means for allowing computer programs or other data or instructions to be loaded into the system 550. Such means may include, for example, an external storage medium 595 and an interface 570. Examples of external storage medium 595 may include an external hard disk drive or an external optical drive, or and external magneto-optical drive.

Other examples of secondary memory 570 may include semiconductor-based memory such as programmable read-only memory ("PROM"), erasable programmable read-only memory ("EPROM"), electrically erasable read-only memory ("EEPROM"), or flash memory (block oriented memory similar to EEPROM). Also included are any other removable storage media 580 and communication interface 590, which allow software and data to be transferred from an external medium 595 to the system 550.

System 550 may also include a communication interface 590. The communication interface 590 allows software and data to be transferred between system 550 and external devices (e.g. printers), networks, or information sources. For example, computer software or executable code may be transferred to system 550 from a network server via communication interface 590. Examples of communication interface 590 include a modem, a network interface card ("NIC"), a wireless data card, a communications port, a PCMCIA slot and card, an infrared interface, and an IEEE 1394 fire-wire, just to name a few.

Communication interface 590 preferably implements industry promulgated protocol standards, such as Ethernet IEEE 802 standards, Fiber Channel, digital subscriber line ("DSL"), asynchronous digital subscriber line ("ADSL"), frame relay, asynchronous transfer mode ("ATM"), integrated digital services network ("ISDN"), personal communications services ("PCS"), transmission control protocol/Internet protocol ("TCP/IP"), serial line Internet protocol/point to point protocol ("SLIP/PPP"), and so on, but may also implement customized or non-standard interface protocols as well.

Software and data transferred via communication interface 590 are generally in the form of electrical communication signals 605. These signals 605 are preferably provided to communication interface 590 via a communication channel 600. In one embodiment, the communication channel 600 may be a wired or wireless network, or any variety of other communication links. Communication channel 600 carries signals 605 and can be implemented using a variety of wired or wireless communication means including wire or cable, fiber optics, conventional phone line, cellular phone link, wireless data communication link, radio frequency ("RF") link, or infrared link, just to name a few.

Computer executable code (i.e., computer programs or software) is stored in the main memory 565 and/or the secondary memory 570. Computer programs can also be received via communication interface 590 and stored in the main memory 565 and/or the secondary memory 570. Such computer programs, when executed, enable the system 550 to perform the various functions of the present invention as previously described.

In this description, the term "computer readable medium" is used to refer to any non-transitory computer readable storage media used to provide computer executable code (e.g., software and computer programs) to the system 550. Examples of these media include main memory 565, secondary memory 570 (including internal memory 575, removable medium 580, and external storage medium 595), and any peripheral device communicatively coupled with communication interface 590 (including a network information server or other network device). These non-transitory computer readable mediums are means for providing executable code, programming instructions, and software to the system 550.

In an embodiment that is implemented using software, the software may be stored on a computer readable medium and loaded into the system 550 by way of removable medium 580, I/O interface 585, or communication interface 590. In such an embodiment, the software is loaded into the system 550 in the form of electrical communication signals 605. The software, when executed by the processor 560, preferably causes the processor 560 to perform the inventive features and functions previously described herein.

The system 550 also includes optional wireless communication components that facilitate wireless communication over a voice and over a data network. The wireless communication components comprise an antenna system 610, a radio system 615 and a baseband system 620. In the system 550, radio frequency ("RF") signals are transmitted and received over the air by the antenna system 610 under the management of the radio system 615.

In one embodiment, the antenna system 610 may comprise one or more antennae and one or more multiplexors (not shown) that perform a switching function to provide the antenna system 610 with transmit and receive signal paths. In the receive path, received RF signals can be coupled from a multiplexor to a low noise amplifier (not shown) that amplifies the received RF signal and sends the amplified signal to the radio system 615.

In alternative embodiments, the radio system 615 may comprise one or more radios that are configured to communicate over various frequencies. In one embodiment, the radio system 615 may combine a demodulator (not shown) and modulator (not shown) in one integrated circuit ("IC"). The demodulator and modulator can also be separate components. In the incoming path, the demodulator strips away the RF carrier signal leaving a baseband receive audio signal, which is sent from the radio system 615 to the baseband system 620.

If the received signal contains audio information, then baseband system 620 decodes the signal and converts it to an analog signal. Then the signal is amplified and sent to a speaker. The baseband system 620 also receives analog audio signals from a microphone. These analog audio signals are converted to digital signals and encoded by the baseband system 620. The baseband system 620 also codes the digital signals for transmission and generates a baseband transmit audio signal that is routed to the modulator portion of the radio system 615. The modulator mixes the baseband transmit audio signal with an RF carrier signal generating an RF transmit signal that is routed to the antenna system and may pass through a power amplifier (not shown). The power amplifier amplifies the RF transmit signal and routes it to the antenna system 610 where the signal is switched to the antenna port for transmission.

The baseband system 620 is also communicatively coupled with the processor 560. The central processing unit 560 has access to data storage areas 565 and 570. The central processing unit 560 is preferably configured to execute instructions (i.e., computer programs or software) that can be stored in the memory 565 or the secondary memory 570. Computer programs can also be received from the baseband processor 610 and stored in the data storage area 565 or in secondary memory 570, or executed upon receipt. Such computer programs, when executed, enable the system 550 to perform the various functions of the present invention as previously described. For example, data storage areas 565 may include various software modules (not shown) that were previously described with respect to FIGS. 2 and 3.

Various embodiments may also be implemented primarily in hardware using, for example, components such as application specific integrated circuits ("ASICs"), or field programmable gate arrays ("FPGAs"). Implementation of a hardware state machine capable of performing the functions described herein will also be apparent to those skilled in the relevant art. Various embodiments may also be implemented using a combination of both hardware and software.

Furthermore, those of skill in the art will appreciate that the various illustrative logical blocks, modules, circuits, and method steps described in connection with the above described figures and the embodiments disclosed herein can often be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled persons can implement the described functionality in varying ways for each particular application, but such implementation decisions should not be interpreted as causing a departure from the scope of the invention. In addition, the grouping of functions within a module, block, circuit or step is for ease of description. Specific functions or steps can be moved from one module, block or circuit to another without departing from the invention.

Moreover, the various illustrative logical blocks, modules, and methods described in connection with the embodiments disclosed herein can be implemented or performed with a general purpose processor, a digital signal processor ("DSP"), an ASIC, FPGA or other programmable logic device, discrete gate or transistor logic, discrete hardware components, or any combination thereof designed to perform the functions described herein. A general-purpose processor can be a microprocessor, but in the alternative, the processor can be any processor, controller, microcontroller, or state machine. A processor can also be implemented as a combination of computing devices, for example, a combination of a DSP and a microprocessor, a plurality of microprocessors, one or more microprocessors in conjunction with a DSP core, or any other such configuration.

Additionally, the steps of a method or algorithm described in connection with the embodiments disclosed herein can be embodied directly in hardware, in a software module executed by a processor, or in a combination of the two. A software module can reside in RAM memory, flash memory, ROM memory, EPROM memory, EEPROM memory, registers, hard disk, a removable disk, a CD-ROM, or any other form of storage medium including a network storage medium. An exemplary storage medium can be coupled to the processor such the processor can read information from, and write information to, the storage medium. In the alternative, the storage medium can be integral to the processor. The processor and the storage medium can also reside in an ASIC.

The above description of the disclosed embodiments is provided to enable any person skilled in the art to make or use the invention. Various modifications to these embodiments will be readily apparent to those skilled in the art, and the generic principles described herein can be applied to other embodiments without departing from the spirit or scope of the invention. Thus, it is to be understood that the description and drawings presented herein represent a presently preferred embodiment of the invention and are therefore representative of the subject matter which is broadly contemplated by the present invention. It is further understood that the scope of the present invention fully encompasses other embodiments that may become obvious to those skilled in the art and that the scope of the present invention is accordingly not limited.

The invention claimed is:

1. A method for standardizing a fluorescence microscopy imaging system, the method comprising:
  by a first imaging system to be standardized, capturing a first normalization image comprising an image of a normalization slide;
  by a reference imaging system, capturing a reference normalization image comprising an image of the normalization slide;
  comparing the first normalization image to the reference normalization image; and
  determining a gamma value and offset value for the first imaging system based on the comparison.

2. The method of claim 1, wherein capturing a first normalization image, comparing the first normalization image to the reference normalization image, and determining a gamma value and offset value for the first imaging system are all performed for each of a plurality of normalization slides.

3. The method of claim 1, wherein the first normalization image and the reference normalization image comprise images of an identical region of the normalization slide.

4. The method of claim 1, further comprising, for the reference imaging system, setting a gamma value to one and an offset value to zero.

5. The method of claim 1, further comprising storing the reference normalization image.

6. The method of claim 1, further comprising by the first imaging system to be standardized,
  capturing a drift image comprising an image of a drift reference slide; and
  calculating a drift measurement using the drift image.

7. The method of claim 6, wherein calculating the drift measurement comprises calculating a ratio of average pixel intensity in the drift image to an exposure of the drift image.

8. The method of claim 6, further comprising:
  by the first imaging system, capturing a digital image of a sample, wherein the digital image comprises a plurality of pixels, each pixel associated with a pixel intensity value; and
  altering one or more of the pixel intensity values based on the drift measurement, the gamma value, and the offset value.

9. The method of claim 8, further comprising storing the digital image without alteration of the pixel intensity values.

10. The method of claim 9, further comprising applying image processing to the digital image, wherein the alteration of one or more pixel intensity values is performed at a time that the application of the image processing is performed.

11. The method of claim 9, further comprising displaying the digital image, wherein the alteration of one or more pixel intensity values is performed at a time that the digital image is displayed.

12. The method of claim 6, further comprising by the reference imaging system, capturing a reference drift image comprising an image of a reference drift slide, and calculating a reference drift measurement using the reference drift image.

13. The method of claim 12, further comprising storing the reference drift measurement.

14. A system for standardizing a fluorescence microscopy imaging system, the system comprising:
  at least one hardware processor; and
  at least one executable module that, when executed by the at least one hardware processor,
    receives a first normalization image comprising an image of a normalization slide captured by the first imaging system,
    receives a reference normalization image comprising an image of the normalization slide captured by a reference imaging system,
    compares the first normalization image to the reference normalization image, and
    determines a gamma value and offset value for the first imaging system based on the comparison.

15. The system of claim 14, wherein the first normalization image and the reference normalization image comprise images of an identical region of the normalization slide.

16. The system of claim 14, wherein at least one executable module, when executed by the at least one hardware processor,
  receives a drift image comprising an image of a drift reference slide captured by a first imaging system, and
  calculates a drift measurement using the drift image.

17. The system of claim 16, wherein calculating the drift measurement comprises calculating a ratio of average pixel intensity in the drift image to an exposure of the drift image.

18. The system of claim 16, wherein the at least one executable module further:
  receives a digital image of a sample captured by the first imaging system, wherein the digital image comprises a plurality of pixels, each pixel associated with a pixel intensity value; and
  alters one or more of the pixel intensity values based on the drift measurement, the gamma value, and the offset value.

19. A non-transitory computer-readable medium having instructions stored thereon, wherein the instructions, when executed by a processor, cause the processor to:
receive a first normalization image comprising an image of a normalization slide captured by a first imaging system;
receive a reference normalization image comprising an image of the normalization slide captured by a reference imaging system;
compare the first normalization image to the reference normalization image; and
determine a gamma value and offset value for the first imaging system based on the comparison.

20. The non-transitory computer-readable medium of claim 19, wherein the first normalization image and the reference normalization image comprise images of an identical region of the normalization slide.

21. The non-transitory computer-readable medium of claim 19, wherein the instructions, when executed by the processor, cause the processor to:
receive a drift image comprising an image of a drift reference slide captured by a first imaging system; and
calculate a drift measurement using the drift image.

22. The non-transitory computer-readable medium of claim 21, wherein calculating the drift measurement comprises calculating a ratio of average pixel intensity in the drift image to an exposure of the drift image.

23. The non-transitory computer-readable medium of claim 21, wherein the instructions further cause the processor to:
receive a digital image of a sample captured by the first imaging system, wherein the digital image comprises a plurality of pixels, each pixel associated with a pixel intensity value; and
alter one or more of the pixel intensity values based on the drift measurement, the gamma value, and the offset value.

* * * * *